(12) United States Patent
MacCraith et al.

(10) Patent No.: US 7,655,475 B2
(45) Date of Patent: Feb. 2, 2010

(54) LUMINESCENCE BASED SENSOR USING PROTUBERANCES TO REDIRECT LIGHT

(75) Inventors: Brian MacCraith, Dublin (IE); Lubos Polerecky, Bremen (DE)

(73) Assignee: Fluorocap Limited, Dublin (IE)

( * ) Notice: Subject to any disclaimer, the term of this patent is extended or adjusted under 35 U.S.C. 154(b) by 679 days.

(21) Appl. No.: 10/470,133

(22) PCT Filed: Jan. 23, 2002

(86) PCT No.: PCT/IE02/00008

§ 371 (c)(1),
(2), (4) Date: Jan. 29, 2004

(87) PCT Pub. No.: WO02/059583

PCT Pub. Date: Aug. 1, 2002

(65) Prior Publication Data

US 2004/0124336 A1 Jul. 1, 2004

(30) Foreign Application Priority Data

Jan. 23, 2001 (IE) .............................. S2001/0051

(51) Int. Cl.
*G01N 21/64* (2006.01)
(52) U.S. Cl. ...................... 436/172; 356/135; 356/136; 356/137; 356/239.2; 356/244; 422/82.05; 422/82.06; 422/82.07; 422/82.08; 422/82.11; 436/164; 436/518

(58) Field of Classification Search .................. 250/339.11–339.12; 356/29.2, 243, 135–137, 356/239.2, 244, 326; 422/82.05–82.08, 82.11; 436/164, 172, 518
See application file for complete search history.

(56) References Cited

U.S. PATENT DOCUMENTS 3,490,847 A * 1/1970 Beale et al. ................. 356/326

(Continued)

FOREIGN PATENT DOCUMENTS

WO WO 98/23945 6/1998

OTHER PUBLICATIONS

Ratner, V. L., Sensors and Actuators, B: Chemical 1994, 17, 113-119.*

(Continued)

*Primary Examiner*—Arlen Soderquist
(74) *Attorney, Agent, or Firm*—Antoinette F. Konski; Foley & Lardner LLP

(57) ABSTRACT

The invention provides a luminescent based sensor having a luminescent material optically coupled to a substrate, and adapted to be used in a medium or environment such as water or air. A detector is provided to detect light that is emitted into the substrate by the material. The substrate is adapted to redirect light that is emitted into the substrate at angles with the range $\theta^{es}_c$ ? $\theta$ ? $\theta^{ls}_c$ where $\theta^{es}_c$ is the critical angle of the environment/substrate interface and $\theta^{ls}_c$ is the critical angle of the luminescent layer/substrate interface. Examples of possible configurations are described.

12 Claims, 15 Drawing Sheets

U.S. PATENT DOCUMENTS

| | | | |
|---|---|---|---|
| 4,602,869 A * | 7/1986 | Harrick | 356/244 |
| 4,608,344 A * | 8/1986 | Carter et al. | 436/34 |
| 4,810,658 A * | 3/1989 | Shanks et al. | 436/172 |
| 4,818,710 A * | 4/1989 | Sutherland et al. | 436/527 |
| 4,826,313 A * | 5/1989 | Schar et al. | 356/51 |
| 4,829,186 A * | 5/1989 | McLachlan et al. | 250/373 |
| 4,839,902 A | 6/1989 | Guch | |
| 5,006,716 A | 4/1991 | Hall | |
| 5,140,393 A * | 8/1992 | Hijikihigawa et al. | 257/252 |
| 5,156,976 A * | 10/1992 | Slovacek et al. | 436/64 |
| 5,192,510 A | 3/1993 | Zoha et al. | |
| 5,268,305 A * | 12/1993 | Ribi et al. | 436/501 |
| 5,440,126 A * | 8/1995 | Kemsley | 250/339.12 |
| 5,512,492 A * | 4/1996 | Herron et al. | 436/518 |
| 5,633,724 A * | 5/1997 | King et al. | 356/445 |
| 5,779,978 A | 7/1998 | Hartmann et al. | |
| 5,841,143 A | 11/1998 | Tuma et al. | |
| 6,128,091 A * | 10/2000 | Uchida et al. | 356/432 |
| 6,690,452 B2 * | 2/2004 | Wilks, Jr. | 356/70 |
| 2003/0157725 A1 * | 8/2003 | Franzen et al. | 436/171 |

OTHER PUBLICATIONS

Lukosz, W., Sensors and Actuators, B: Chemical 1995, 29, 37-50.*
Gao, H. H. et al, Optical Engineering 1995, 34, 3465-3470.*
Neuschafer, D., et al, SPIE 1996, 2836, 221-234.*
Doyle, A. et al, SPIE 1997, 3105, 61-70.*
Kunz, R. E., Sensors and Actuators, B: Chemical 1997, 38, 13-28.*
Gouin, J.-F. et al, Electronics Letters 1998, 34, 1685-1687.*
Rowe, C. A. et al, Analytical Chemistry 1999, 71, 433-439.*
Plowman, T. E. et al, SPIE 1999, 3603, 163-169.*
Feldstein, M. J. et al, Biomedical Microdevices 1999, 1, 139-153.*
Kim, Y.-J. et al, Japanese Journal of Applied Physics, Part 1: Regular Papers, Short Notes & Review Papers 2000, 39, 1538-1541.*
Zeller, P. N. et al, Biosensors & Bioelectronics 2000, 15, 591-595.*
Yang, R. et al, SPIE 2000, 4092, 155-157.*
Polerecky, L. et al, Applied Optics 2000, 39, 3968-3977.*

* cited by examiner

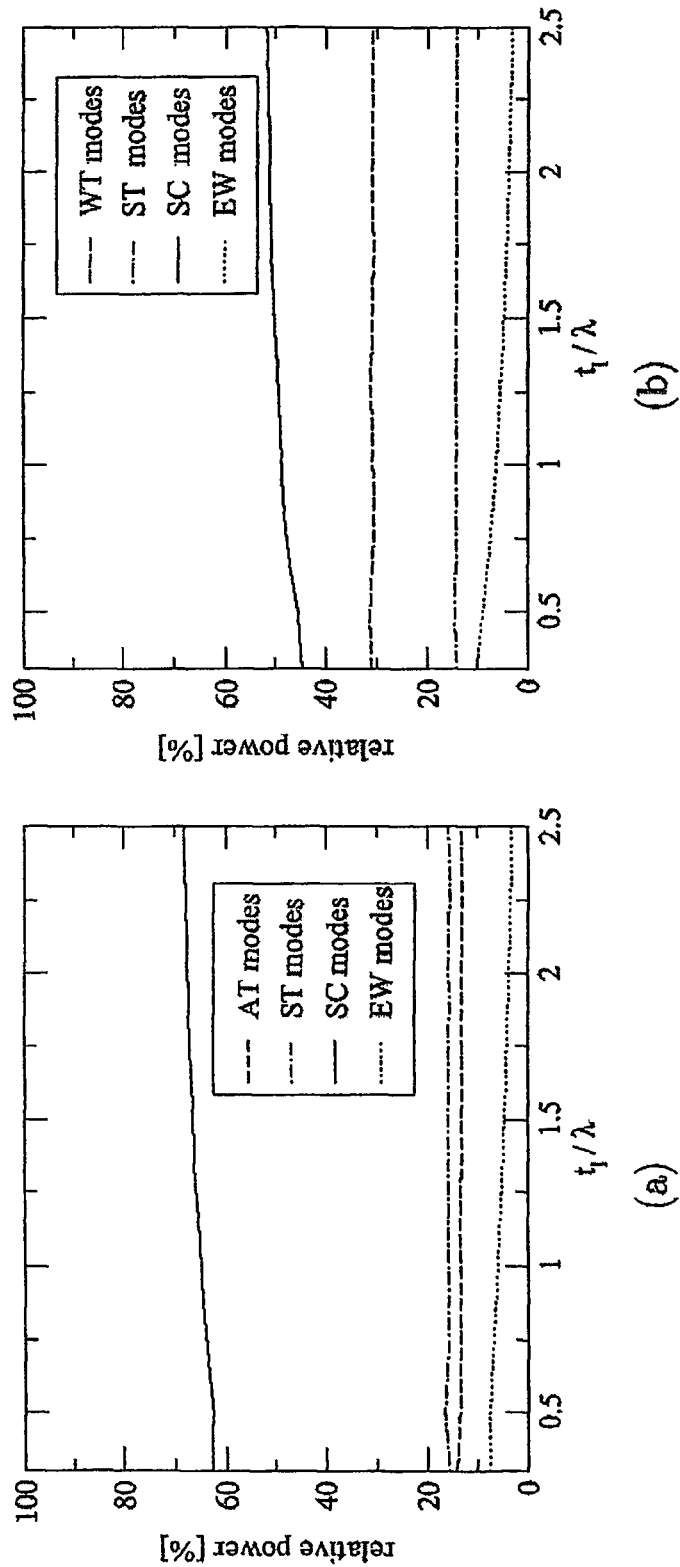
Figure 4.1

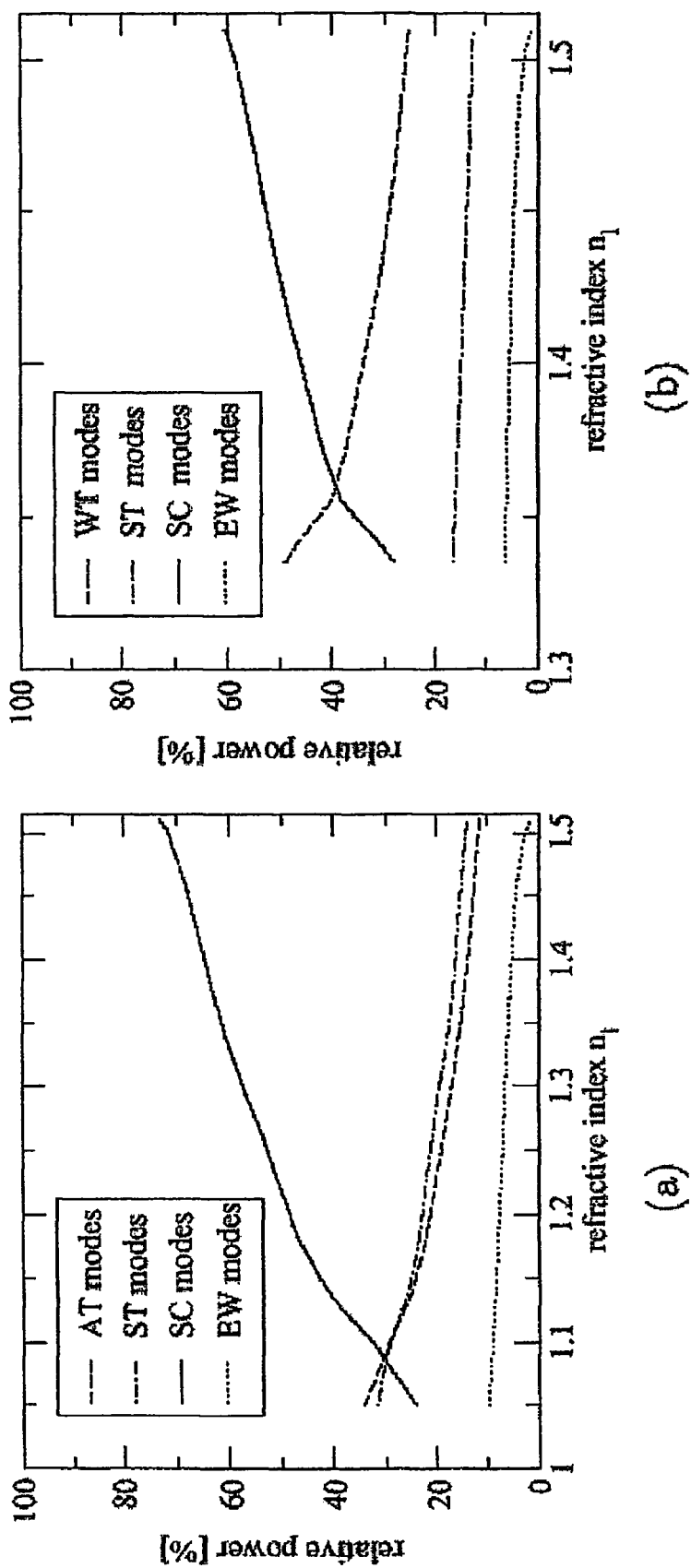
Figure 4.2

LUMINESCENCE BASED SENSOR USING PROTUBERANCES TO REDIRECT LIGHT

CROSS-REFERENCE TO RELATED APPLICATION

This application is a national stage application under 35 U.S.C. §371 of International Application No. PCT/IE02/00008, filed Jan. 23, 2002, which in turn claims priority to IE Application No. S2001/0051, filed Jan. 23, 2001.

FIELD OF THE INVENTION

The present invention relates to a luminescence based sensor or sensor configuration of the type comprising a substrate, an emitting layer having a luminescence material which on stimulation is adapted to transmit luminescence into the substrate and a detector for detecting light subsequently transmitted out of the substrate.

BACKGROUND TO THE INVENTION

There has been increasing application of luminescence based sensors in areas such as environmental monitoring, biochips, DNA chips, bioluminescence, chemiluminescence and many others. The sensors typically comprise a substrate having a luminescence emitter in optical contact therewith. The emitter may of itself transmit luminescence into the substrate or may require to be activated in some way, either by incident light or by some chemical reaction. There are various forms of luminescence: phosphorescence which is long lived light transmission, fluorescence which is short lived, chemiluminescence where two chemicals react and finally bioluminescence. Within the present specification the term "luminescence" is intended to encompass all such forms of luminescence. Many chemical sensors and biosensors are based on the luminescence emitted from thin layers or patterned arrays of fluorophores deposited on a dielectric interface such as a waveguide surface or a transparent substrate. One of the key issues in these sensors is the efficiency of the luminescence collection.

A typical configuration in many luminescence-based sensor applications involves a thin luminescent film or spot deposited onto a planar substrate. An example of such a configuration is FIG. 1, which shows a substrate 100 having a luminescent spot 110 deposited thereon. A detector 120 is provided under the substrate 100 and is adapted to detect light 130 that is transmitted by the spot into the substrate and which passes out of the substrate. It will be noted that the detector is positioned directly under the spot 110 so as to detect light that passes normally (i.e. undeviated by refraction at the interfaces) through the substrate. Within the present specification the element containing the substrate and the luminescent layer or spot will be referred to as the sensing element or sensor chip. The sensor chip is considered to be designed independently of the sensor system in which it is to be incorporated.

A majority of luminescence-based sensor systems employ rather inefficient techniques for the collection of luminescence emitted by a thin sensing film or molecules attached to a surface. A number of authors have developed new ways of dealing with the issue of low luminescence intensity emitted by systems under study. Liebermann et al. [*T. Liebermann and W. Knoll. Surface-plasmon field-enhanced fluorescence spectroscopy. Colloids and Surfaces, A: Physicochemical and Engineering Aspects* 171:115-130, 2000.] exploited the enhancement of the amplitude of the excitation light in the close vicinity of a metal surface provided by the efficient excitation of the surface plasmon wave. Blair & Chen [*S. Blair and Y Chen. Resonant-enhanced evanescent-wave fluorescence biosensing with cylindrical optical cavities. Applied Optics*, 40(4):570-581, 2001] showed that luminescence of molecules can be enhanced by the use of planar cylindrical resonant optical cavities.

It is also known to incorporate metal coatings or metal nanoparticles into a sensor and the incorporation of these materials can have a very positive influence on the intensity of luminescence emitted by molecules located in their close vicinity. Enhancement of the quantum yield in the order of 100-1000 has been reported. Although these developments are certainly valuable for the improvement of the performance of the luminescence-based chemical sensors and biosensors, they do not address the issue of efficiency of the luminescence collection.

Polerecky L et al (*Applied Optics* 39 (22): 3968-3977 Aug. 1, 2000) have described a theory of radiation from dipoles embedded inside an arbitrary multilayer system . They derive explicit expressions for the angular distribution of the electromagnetic field and intensity radiated by the dipole into the surrounding media. Using this theoretical analysis they conclude consequences for optimisation of optical chemical sensors and biosensors based on luminescence emission, specifically that as a large proportion of the luminescence is radiated into the higher refractive index substrate and due to total internal reflection at the glass/air interface is guided along the glass-slide, better results should be provided by detecting the luminescence at the edge of the glass-slide. Although this technique facilitates the detection of the modes that normally propagate along the glass slide towards the edge, the detection is not optimised, as only those modes propagating within a narrow angular range $\Delta\phi$, as shown in FIG. 2, are detected. In order to maximise this fraction, detectors would have to be placed all around the substrate which is not feasible in most practical applications.

There therefore exists a need for a method and sensor for detecting a luminescence signal that is based on the understanding that a large proportion of luminescent light that is radiated into a substrate to which the material is attached is not detected.

OBJECT OF THE INVENTION

It is an object of the present invention to provide a sensor configuration which is adapted to detect light that is radiated into a substrate at high angles. It is also an object of the present invention to provide a method of detecting the presence of analytes using sensor configurations that are optimised for detecting light that is radiated into a substrate at such high angles.

SUMMARY OF THE INVENTION

Accordingly the present invention provides a luminescent sensor configuration comprising a substrate having a first refractive index, a luminescent material having a second refractive index and a detector. The sensor is adapted for use in a medium having a third refractive index; the third refractive index being less than the second refractive index and the second refractive index being less than the first refractive index, The substrate is adapted to specifically redirect light radiated into the substrate by the luminescent material at angles which are less than the critical angle of the luminescent material/substrate interface and greater than the critical angle of the medium/substrate interface, the light being redirected out of the substrate and towards a detector.

Desirably at least two distinct portions of luminescent material are provided each portion being optically coupled to the substrate. The substrate is typically adapted to redirect the light emitted by each portion towards the detector such that the light received at the detector from a first portion is spatially independent from the light received at the detector from a second portion.

The redirection of light by the substrate is preferably effected by at least one optical redirection element provided at either upper or lower surfaces of the substrate.

In a first embodiment the at least one optical redirection element is adapted to redirect the light using total internal reflection.

Such a configuration may comprises a plurality of optical redirection elements, each element comprises a frusto-conical structure raised above the upper surface of the substrate, each frusto-conical structure having side walls and an upper surface, luminescent material being carried on the upper surface of the structure, and wherein light emitted by the material into the structure is internally reflected by the side walls of the structure and directed towards a detector positioned beneath the substrate.

It may alternatively comprises at least one ridge raised above the upper surface of the substrate and extending along the upper surface of the substrate, the ridge having side walls and an upper surface, luminescent material being carried on the upper surface of the ridge, and wherein light emitted by the material into the ridge is internally reflected by the side walls of the ridge and directed towards a detector positioned beneath the substrate.

The side walls of the redirection element are typically vertically displaced from the upper surface of the redirection element at an angle substantially equivalent to one quarter the sum of the critical angles of the luminescent material/substrate interface and the medium/substrate interface.

In an alternative embodiment the at least one optical redirection element is adapted to redirect the light using refraction.

In such an embodiment the at least one optical redirection element may comprise a prism optically coupled to a lower surface of the substrate, the prism being adapted to receive light incident on the lower surface of the substrate and redirect that light sidewardly towards a detector.

It may alternatively comprise a plurality of prisms, each prism being associated with a unique spot on the upper surface of the substrate, such that light emitted by a spot is received within its associated prism and re-directed towards a detector.

The prism is typically optically coupled to the lower surface of the substrate and the prism has the same refractive index as the substrate to which it is optically coupled.

In a further embodiment the at least one optical redirection element is adapted to redirect the light using diffraction. Typically this comprises a diffractive optical element provided at the lower surface of the substrate.

In an alternative embodiment the lower surface of the substrate is structurally configured to both reflect and refract light radiated into the substrate, the reflection and refraction of the light effecting a redirection of light towards a detector. In such an embodiment the lower surface is typically such as to provide a first surface on which light emitted from the material and incident thereon is refracted out of the substrate and towards the second surface, which reflects the light which is incident thereon towards the detector.

In yet a further embodiment the optical redirection element comprises a refractive index barrier extending inwardly of the substrate, the refractive index barrier being substantially perpendicular to the lower surface of the substrate such that light incident on the barrier from the luminescent material is reflected downwardly and out of the substrate. Typically the refractive index barrier comprises an annular slot having side walls, the side walls extending inwardly of the substrate, the walls being substantially perpendicular to the lower surface of the substrate such that light that is incident on the walls from the luminescent material is reflected downwardly and out of the substrate.

The walls may be provided with a reflective coating so as to improve the reflectivity of the surfaces of the walls. Such a reflective coating is typically formed from metal particles or material deposited on the walls.

In yet a further embodiment the redirection of light by the substrate is effected by providing the substrate with nonparallel upper and lower surfaces, the angle of the upper and lower surfaces being such that the light emitted by the luminescence material is incident on the surfaces at angles greater than the critical angle of the substrate/medium interface, thereby effecting a propagation of light along a critical axis of the substrate towards a detector.

The sensor configuration is typically configured such that the detector detects light radiated into the substrate by the luminescent material at angles which are not less than the critical angle of the luminescent material/substrate interface and greater than the critical angle of the medium/substrate interface, in addition to the light radiated within the angular range.

The detector is desirably a CMOS or CCD type detector.

The luminescent material is desirably sensitive to an analyte with which the sensor is intended to be used. The presence of an analyte in the medium with which the sensor is used effects a luminescence of the material and said luminescence is detected at the detector.

The sensor configuration may be initially provided with a bio-recognition element, the bio-recognition element being sensitive to and adapted to couple with any compatible biological sample in the medium with which the sensor is used. Once this coupling has been effected the sensor may be exposed to a luminescent tag which couples to the coupled biological sample/bio-recognition element so as to radiate luminescence into the substrate.

The invention additionally provides a luminescence sensor comprising a substrate adapted to receive incident light emitted from a luminescence material optically coupled thereto, a detector adapted to detect the light emitted into the substrate and wherein the substrate is specifically adapted to outwardly direct light defined by the substrate confined (SC) modes of the incident light from the substrate and towards the detector.

The structural geometry of the substrate at the upper or lower surfaces thereof is desirably such as to the outwardly direct the light defined by the SC modes.

The invention additionally provides an assay tool for use in detecting the presence of a substance in a medium, the tool comprising a substrate having at least one optical redirection element at either upper or lower surfaces of the substrate, the optical redirection element adapted to specifically redirect light radiated into the substrate by a luminescent material at angles which are less than the critical angle of the luminescent material/substrate interface and greater than the critical angle of the medium/substrate interface, the light being redirected out of the substrate and towards a detector.

The invention may additionally provide a method of enhancing the luminescence capture from an assay tool, the method comprising the step of providing an assay tool having a substrate with at least one optical redirection element at either upper or lower surfaces of the substrate, the optical redirection element adapted to specifically redirect light radiated into the substrate by a luminescent material at angles which are less than the critical angle of the luminescent material/substrate interface and greater than the critical angle of the medium/substrate interface, the light being redirected out of the substrate and towards a detector.

In a further embodiment the invention provides a luminescence-based sensor of the type comprising a substrate mounting an emitting layer transmitting luminescence into the substrate and a detector for measuring some of the trapped light in the substrate subsequently transmitted out of substrate characterised in that the substrate is so configured to internally direct the trapped light through an exit surface to the detector.

By configuring the substrate externally i.e. by altering its shape, it is possible to ensure that the trapped light is directed to an exit surface and is not totally internally reflected within the substrate. The detector could, for example, be a photo detector which may be a CCD camera which can be located below or above the substrate. The invention arises out of an analysis of the radiation of dipoles placed within a thin dielectric layer coated on a higher refractive index substrate which reveals that the luminescence exhibits strong spatial anisotropy with significantly greater amounts of luminescence radiated within a certain interval of angles.

Accordingly the invention provides a range of configurations which exploit the findings that a significantly greater amount of luminescence is radiated into the higher refractive index substrate at angles greater than the critical angle of the substrate/superstrate interface, and that in most substrates, most of the luminescence is radiated into the substrate and is trapped there and ensures that the luminescence, instead of being trapped within the substrate, is transmitted out of it for subsequent detection and measurement.

In one embodiment of the invention, the luminescence-based sensor is so arranged that the trapped light is directed through the exit surface substantially normally thereto.

In another embodiment of the invention, at least either the upper surface mounting the emitter or the lower surface of the substrate is not planar. If planar, the surfaces are not parallel.

In a further embodiment of the invention, the interfaces of the substrate are so configured that the internal reflection at the interface on which the trapped light impinges is substantially prevented and allows the light to be transmitted through the substrate.

In yet another embodiment of the invention, the interfaces of the substrate are so configured that the trapped light is reflected from at least one interface before being directed out of the substrate to the detector.

These and other features of the present invention will be better understood with reference to the following drawings

DETAILED DESCRIPTION OF THE DRAWINGS

Figure 1:
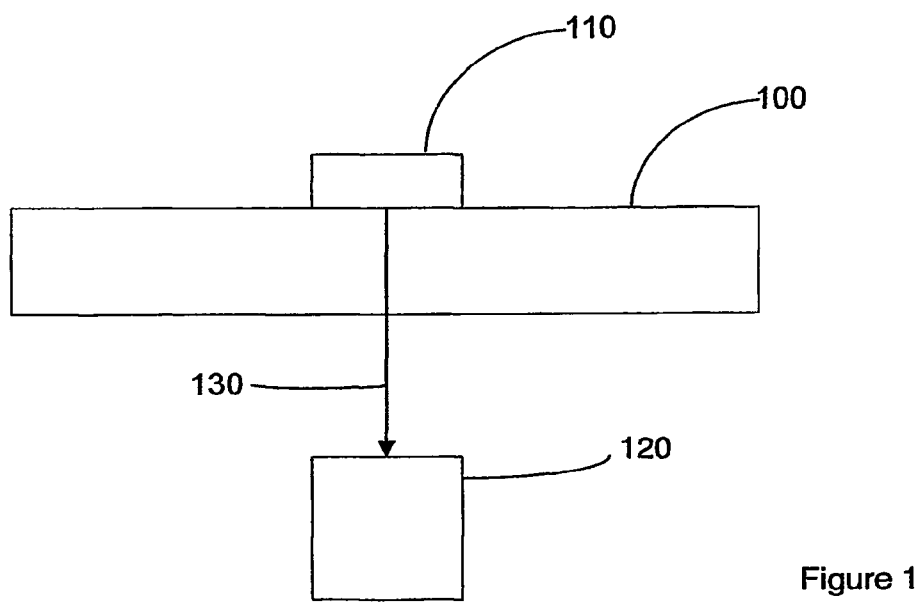
FIG. 1 is a schematic showing a sensor device according to the prior art.
Figure 2:
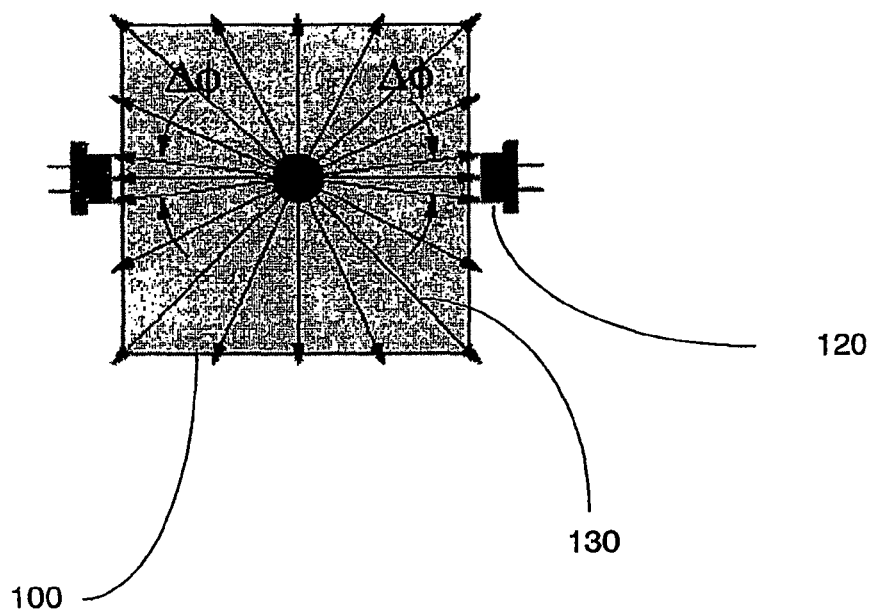
FIG. 2 shows a configuration-adapted for edge detecting light passing out through the edges of a substrate.

FIGS. 1 and 2 have been described with reference to the prior art.

The present invention utilises light that is transmitted into the substrate by a luminescent material at high incident angles. Using conventional prior art apparatus such light has propagated within the substrate and although it has been noted that a portion of it passes out through edge portions of the substrate a method and apparatus that is specifically adapted to detect such modes of light has hereintobefore not been described.

Figure 3:
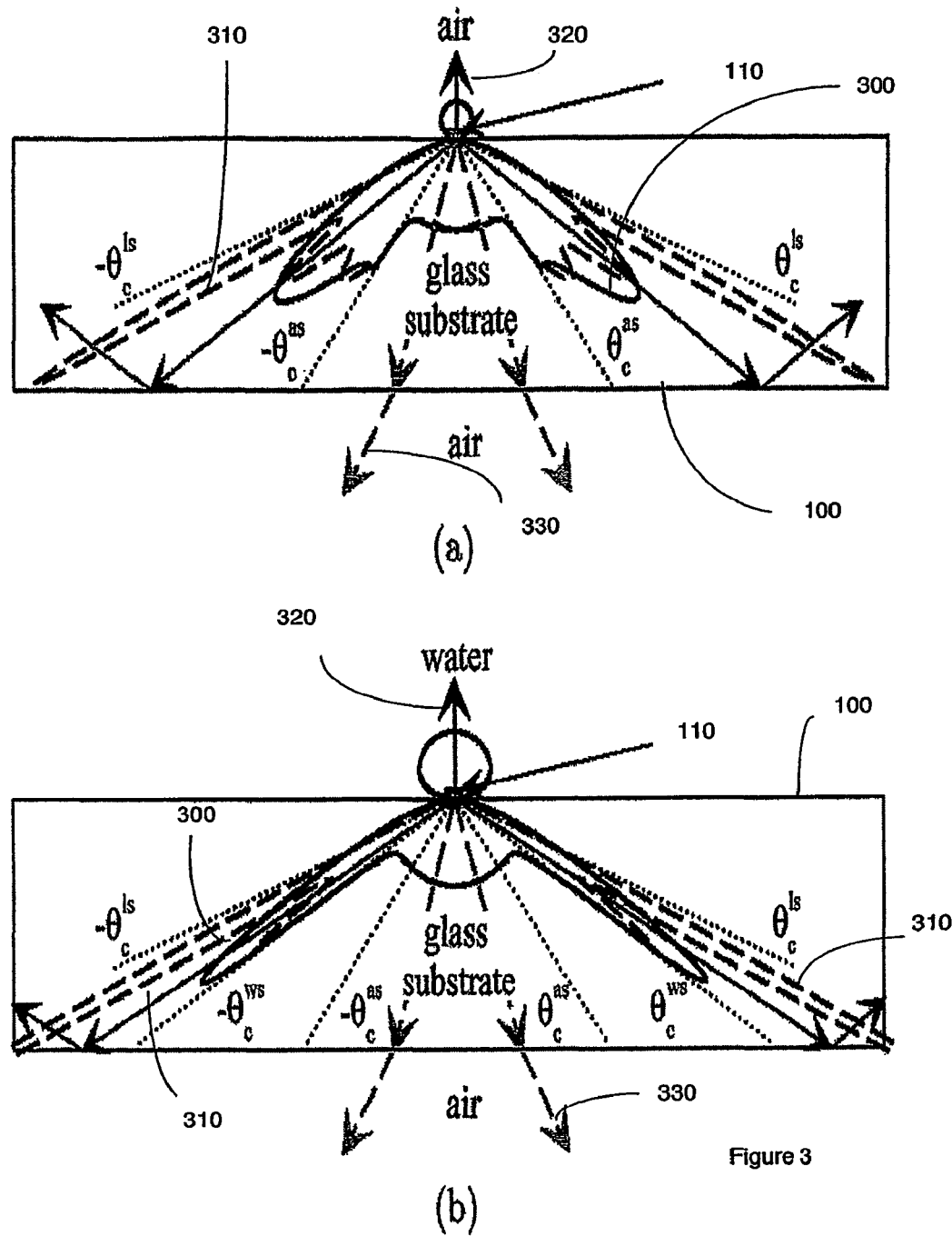
FIG. 3 shows the angular properties of luminescence radiated from a small luminescence spot on a glass substrate; the substrate being surrounded by air below and by air above (FIG. 3a) and by water above (FIG. 3b), FIG. 4.1(a) is a graph showing the relative optical power carried by the AT, ST, SC and EW modes as a function of the thickness $t_l$ of the luminescent spot, while the refractive index of the layer is constant an equal to $n_l$=1.43 and the spot is covered by air, FIG. 4.1(b) is equivalent to FIG. 4.1(a) but when the spot is covered with water and the AT modes are substituted by WT modes, FIG. 4.2(a) is a graph showing the relative optical power carried by the AT, ST, SC and EW modes as a function of the refractive index $n_l$ of the luminescent spot, while the thickness of the layer is constant an equal to $t_l$=1:5λ, and the spot is covered by air, FIG. 4.2(b) is equivalent to FIG. 4.2(a) but when the spot is covered by water, and the AT modes are substituted by WT modes.

FIG. 3 shows an example of a sensing element. The same reference numerals will be used for the same components in the various embodiments. It consists of a "thick" glass slide substrate 100 (refractive index $n_s$=1.515, thickness~1 mm) on top of which a small spot of luminescent material 110 (refractive index $n_l$=1:43) is deposited. It will be appreciated that the material is optically coupled to the substrate. By the term optically coupled it will be appreciated by those skilled in the art that it encompasses a plurality of different arrangements including, but not limited to:

i. luminescent molecules directly bound to or adsorbed on substrate, ii. luminescent molecules indirectly attached to substrate via one or more linker molecules (such as in a sandwich assay), iii. luminescent molecules entrapped/contained within a thin film, for example a polymer or sol-gel matrix, coated on substrate.

The thickness $t_l$ of the layer forming the spot is assumed to be uniform and in the range of hundreds of nanometers. Furthermore, for simplicity, the size of the spot is assumed to be small compared to the size of the area of the detection system which is used to detect the luminescence produced by the spot. The latter restriction is assumed only to ensure that the luminescent spot "appears" to the detector as a spot rather than as an area over which the radiated intensity would have be integrated. Consequently, the lateral (x-y) dimensions do not have to be considered and only the angular dependence of the radiated intensity needs to be taken into account in the following analysis. The luminescent spot is assumed to be covered by the environment, which is either air ($n_a$=1.0) or water ($n_w$=1.33). The slide is surrounded by air from below.

The predicted angular distribution of the luminescence emerging from the small luminescent spot deposited on the glass substrate is shown in FIG. 3. The graphs (a) and (b) correspond to the situations where the environments or media covering the spot are air and water, respectively. In both graphs, the solid line 300 and the dashed line 310 correspond to the thickness of the luminescent spot equal to $t_l$=0.5λ and $t_l$=1.5 λ, respectively, where λ is the luminescence wavelength. Luminescence that can be detected by the detector placed above the glass substrate is schematically shown by the arrow 320. Luminescence within this angular distribution is typical of the luminescence that has traditionally been used within sensor systems. As can be seen from the displacement of the luminescence as shown in the solid 300 or dashed 310 lines located in air or water above the glass substrate, the amount of luminescence radiated into the environment covering the spot is relatively small.

The situation is similar when the detector is placed below the glass substrate. Due to reflections taking place at the bottom glass/air interface, the light impinging at this interface is transmitted to air only if the incident angle lies within the angular range $\theta \in <-\theta_c^{as}, \theta_c^{as}>$, where $\theta_c^{as}$=arcsin($n_a/n_s$)≈ 41.3° is the critical angle of the substrate (glass)/air interface. This light is schematically depicted by the dashed arrows 330. Due to the refraction, the light propagating inside the substrate at angles $\theta \in <-\theta_c^{as}, \theta_c^{as}>$ is partially transmitted into the air under the substrate at angles $\theta \in <-90°, 90°>$. The solid 300 and dashed 310 lines within the angular range $\theta \in <-\theta_c^{as}, \theta_c^{as}>$ demonstrate that the amount of luminescence transmitted to air below the glass substrate is also relatively small. These arrows indicate the portion of the light that is traditionally detected using prior art apparatus.

The light propagating inside the substrate at angles greater than the critical angle $\theta_c^{as}$ is totally reflected at the lower substrate/air interface. If the environment covering the slide is air, as shown in FIG. 3(a), this light is also totally reflected at the upper layer/air interface and is effectively trapped (or confined) within the waveguiding glass substrate. If the environment above the slide is water, as shown in FIG. 3(b), the part of the light propagating in the substrate at angles $\theta \in <\theta_c^{as}, \theta_c^{ws}>$ and $\theta \in <-\theta_c^{as}, -\theta_c^{ws}>$ is partially transmitted into water and partially reflected back to the substrate. Furthermore, the part of light propagating at $\theta \in <\theta_c^{ws}, 90°>$ and $\theta \in <-\theta_c^{ws}, -90°>$ is totally reflected at the upper layer/water interface. In any case, due to the relation $\theta_c^{ws} > \theta_c^{as}$, the light exhibiting the enhanced intensity is always trapped inside the substrate due to the total internal reflection at both the upper and lower interfaces. This light has previously not been captured in prior art arrangements and has propagated normally within the substrate until it escapes out the edges of the substrate.

This analysis clearly explains why large values of the luminescence capture efficiency cannot be achieved by the conventional detection technique employing detection above or below the substrate. It is mainly due to the fact that conventional techniques facilitate the detection only of the low-intensity modes generated by the luminescent spot. The analysis also demonstrates that a higher capture efficiency could be achieved if the more intense modes, i.e., those propagating at angles $\theta \in <\theta_c^{es}, \theta_c^{ls}>$ and $\theta \in <-\theta_c^{es}, -\theta_c^{ls}>$ are detected. In these expressions, $\theta_c^{es}$ is equal either to $\theta_c^{as}$ or $\theta_c^{ws}$ depending on whether the environment covering the luminescent spot is air or water, and $\theta_c^{ls}$ is the critical angle of the layer/substrate interface.

To simplify the subsequent discussion, the following terminology is introduced. The luminescence directly transmitted to air or water above the substrate will be called "the air-transmitted" or "the water-transmitted luminescence". The corresponding modes of the electromagnetic field will be called "the air-transmitted" or "water-transmitted modes" or, shortly, AT or WT modes. The luminescence radiated into the substrate at angles $\theta \in <-\theta_c^{as}, \theta_c^{as}>$, which is eventually transmitted into air under the substrate, will be called "the substrate-transmitted luminescence". The corresponding modes will be called "the substrate-transmitted (ST) modes". The luminescence radiated into the substrate at angles $\theta \in <\theta_c^{es}, \theta_c^{ls}>$ and $\theta \in <-\theta_c^{es}, -\theta_c^{ls}>$, which is trapped or confined inside the substrate, will be called "the substrate-confined luminescence". The corresponding modes will be called "the substrate-confined (SC) modes". The luminescence propagating at angles $\theta \in <\theta_c^{ls}, 90°>$ and $\theta \in <-\theta_c^{ls}, -90°>$ will be called "the evanescent-wave (EW) luminescence". The corresponding modes will be called "the evanescent-wave (EW) modes". Although it is also trapped (confined) inside the substrate, this name reflects better the character of the field corresponding to these modes, which is evanescent in the luminescent layer. This is qualitatively different from the SC modes, whose field is propagating (i.e., described by a harmonic function) inside the luminescent layer.

Figure 5:
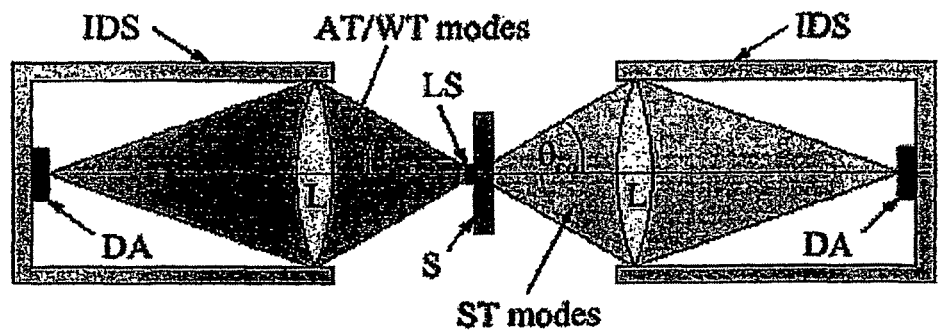
FIG. 5 is a schematic diagram of an ideal detection system (IDS) characterised by a numerical aperture NA=sin $\theta_{co}$, where $\theta_{co}$ is the cone angle associated with the cone of light entering the system.

To provide quantitative analysis of the improvement in the luminescence capture efficiency that could be achieved by employing the detection of the SC modes in accordance with the present invention, the total optical power carried by the AT/WT modes, ST modes, SC modes and the EW modes may be calculated and compared. Such a comparison is shown in FIGS. 4 and 5. The graphs (a) and (b) in both figures correspond to the situations where the environments covering the luminescent spot are air and water, respectively.

FIG. 4.1 shows the relative power carried by the modes as a function of the thickness $t_l$ of the luminescent layer, where the refractive index of the layer is assumed to be constant and equal to $n_l$=1.43. The total power carried by all the modes is proportional to the thickness $t_l$. However, as can be seen from both graphs in FIG. 4.1, the relative fraction of the power carried by each of the modes remains practically constant over a substantially large interval of $t_l$. The notable variation is exhibited by the SC modes which gain the relative power at the expense of the EW modes. This is due to the fact that for greater values of $t_l$ the coupling between the more distant regions of the luminescent layer from the substrate and the EW modes is weaker (due to the finite penetration depth of the evanescent field). The graph (a) in FIG. 4.1 indicates that the SC modes carry approximately 66% of the total luminescence radiated by the spot when the spot is covered by air. This number is somewhat smaller when the luminescent spot is covered by water (approx. 50%), which is caused by the increase of the fraction of luminescence radiated into water by means of the WT modes, as follows from the comparison of the dashed lines in graphs (a) and (b).

Although these numbers might not seem too large when compared to the fractions of the power carried by the AT modes (approx. 15%), WT modes (approx. 30%) or the ST modes (approx. 15%), it is important to realise that the SC modes are "localised" in a narrower angular range ($\Delta\theta=\theta_c^{ls}-\theta_c^{as}\approx 30°$ and $\Delta\theta=\theta_c^{ls}-\theta_c^{ws}\approx 10°$ for the situations where the spot is covered by air and water, respectively) than the other modes, which are propagating in the full range $\theta \in <-90°, 90°>$. To facilitate the detection of the full power carried by the AT, WT, or ST modes, one would have to use a detection system with the value of the numerical aperture equal to 1, which is difficult to achieve. On the other hand, the large power carried by the SC modes could be detected using a detection system with a low value of the numerical aperture (not exceeding sin 15°≈0.26 for $\Delta\theta=30°$ or sin 5°≈0.09. for $\Delta\theta=10°$).

FIG. 4.2 shows the relative power carried by the modes as a function of the refractive index $n_l$ of the luminescent layer, where the layer thickness is assumed to be constant and equal to $t_l=1.5\lambda$. It can be seen that the power carried by the SC modes increases rapidly as $n_l$ approaches the value of the substrate refractive index ($n_s=1.515$). This is mainly due to the shift of the critical angle, which converges to 90° as $n_l$ approaches $n_s$. As in the case discussed above, the fraction of the power carried by the SC modes is generally smaller when the environment covering the luminescent spot is water. This is again due to the fact that the luminescence radiated into water has higher intensity, as follows from the comparison of the dashed lines in the graphs (a) and (b) of FIG. 4.2.

Nevertheless, FIG. 4.2 demonstrates that a greater fraction of the energy carried by the SC modes is obtained when the refractive index of the luminescent layer is chosen as close to that of the substrate as possible. The above analysis considers the total optical power carried by the various types of modes radiated from the luminescent spot. This means that in order to make these quantities comparable as measures of the luminescence capture efficiency, a detection system which is able to capture all the power carried by the particular modes would have to be employed. For example, in case of the AT, WT or ST modes, the detection system would have to be able to detect light beams propagating in the cone with the cone angle of 90°, i.e., characterised by the numerical aperture NA=1.

In order to provide a better quantitative comparison between the different types of modes, it is necessary to consider them in the context of the detection system. This can be done by evaluating the detected power as a function of the numerical aperture of the detection system. In the following analysis, an ideal detection system, which is depicted in FIG. 5, is considered. It is assumed to be placed directly below or above the luminescent spot, i.e., its axis (dashed-dotted line) is perpendicular to the surface of the substrate and intersects the luminescent spot. The system employs an ideal lens (L) which redirects the beams corresponding to the AT/WT and ST modes to the detector array (DA). S denotes the substrate containing the luminescent spot (LS), as shown in FIG. 3.

Figure 6:
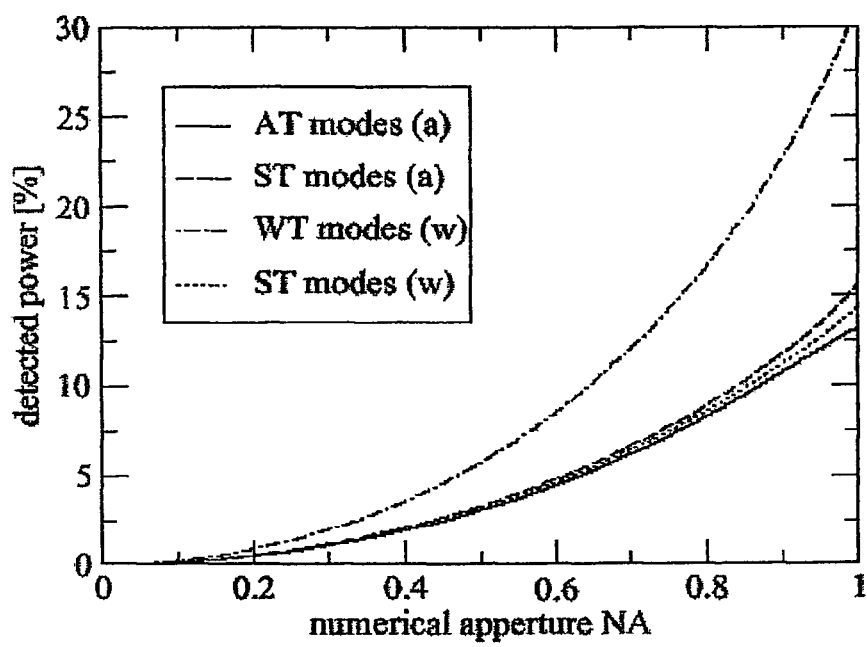
FIG. 6 is a graph showing the efficiency of the detection of optical power carried by various types of modes radiated by the luminescent spot as plotted for the ideal situation of FIG. 5 as a function of its numerical aperture NA.

One of the most important quantities characterising a detection system is its numerical aperture (NA). It is related to the value of the cone angle $\theta_{co}$ by NA=sin $\theta_{co}$. The fact that the system is ideal means that all the light propagating within the cone characterised by the cone angle $\theta_{co}$=arcsin NA is detected and converted to the signal proportional to the total power carried by the corresponding modes. At this stage, only the AT, WT and ST modes are considered. FIG. 6 shows the efficiency of detection of the AT, WT and ST modes as a function of the numerical aperture of the ideal detection system described above. The lines marked by (a) and (w) correspond to the situations where the luminescent spot is covered by air and water, respectively.

TABLE 1

Relative values of total optical power carried by specified modes calculated for a sensor chip depicted in FIG. 3. The thickness and refractive index of the luminescent spot for which these values were calculated are $t_l=1.5\lambda$ and $n_l=1.43$, respectively.

| luminescent spot covered by | |
|---|---|
| air | water |
| AT modes: ≈13% | WT modes: ≈31% |
| ST modes: ≈16% | ST modes: ≈14% |
| SC modes: ≈66% | SC modes: ≈50% |
| EW modes: ≈5% | EW modes: ≈5% |

It can be seen from the graph of FIG. 6 that the relative values of the detected optical power, which are listed in Table 1, can be achieved only with a detection system whose numerical aperture is equal to unity. For NA<1, the capture efficiency decreases rapidly. For example, it falls below 5% for NA<0.5. This means that even an ideal detection system cannot detect more than 5% of the total power radiated by the luminescent spot when its numerical aperture is lower than 0.5. This makes the SC modes attractive because they carry more power which is concentrated within a narrower angular range, thus allowing for a greater capture efficiency at a lower numerical aperture of the detection system.

It will be appreciated by those skilled in the art that the above numerical analysis has been conducted with reference to specific exemplary values of the refractive index and the thickness of the luminescent layer and other material involved. The present invention is not intended to be limited to any such specific example and it will be further appreciated that a similar analysis with qualitatively similar results is obtainable for any other set of parameters.

It will be further appreciated from the previous discussion that the modes that we are mainly interested in, in accordance with the present invention, are those modes radiated into the higher refractive index substrate at angles $\theta$ that satisfy the following inequalities:

$$\theta_c^{es} < \theta < \theta_c^{ls} \qquad (1)$$

where $\theta_c^{es}$ is the critical angle of the environment/substrate interface and $\theta_c^{ls}$ is the critical angle of the luminescent layer/substrate interface. It will be appreciated that the term "environment" is intended to define the medium such as air or water where the sensor is used. If the refractive indices of the substrate, luminescent layer and environment are denoted as $n_s$, $n_l$ and $n_e$, respectively, the critical angles are calculated as:

$$\theta_c^{es} = \arcsin(n_e/n_s), \qquad (2a)$$

$$\theta_c^{ls} = \arcsin(n_l/n_s), \qquad (2b)$$

The inequality (1) requires that the refractive indices must satisfy the relation $$n_e < n_l < n_s. \qquad (3)$$

It should be noted that the enhancement effects that are exploited according to the present invention occur if the refractive indices characterising the materials satisfy the relation (3).

Using an appreciation of the mechanism of propagation of a luminescence radiated from a luminescent spot or layer by the SC modes, the present invention provides means by which these modes may be detected so as to improve luminescence capture efficiency. The present invention provides in preferred embodiments for a modification of the geometry of the top or bottom interface or surface of the substrate so as to re-direct the SC modes towards a detector placed either above or below the substrate. This modification can be achieved by a plurality of different mechanisms, examples of which will be illustrated in the following sections. It will be appreciated that by employing macroscopic or microscopic structures at the top or bottom substrate interface that is possible, using for example means of reflection, refraction or diffraction to change the direction of propagation of the SC modes. Such a redirection may be adapted to effectively direct the SC modes towards a suitably orientated detector.

The following examples are presented as exemplary embodiments of the present invention and are not intended to limit the invention to such embodiments.

Figure 7A:
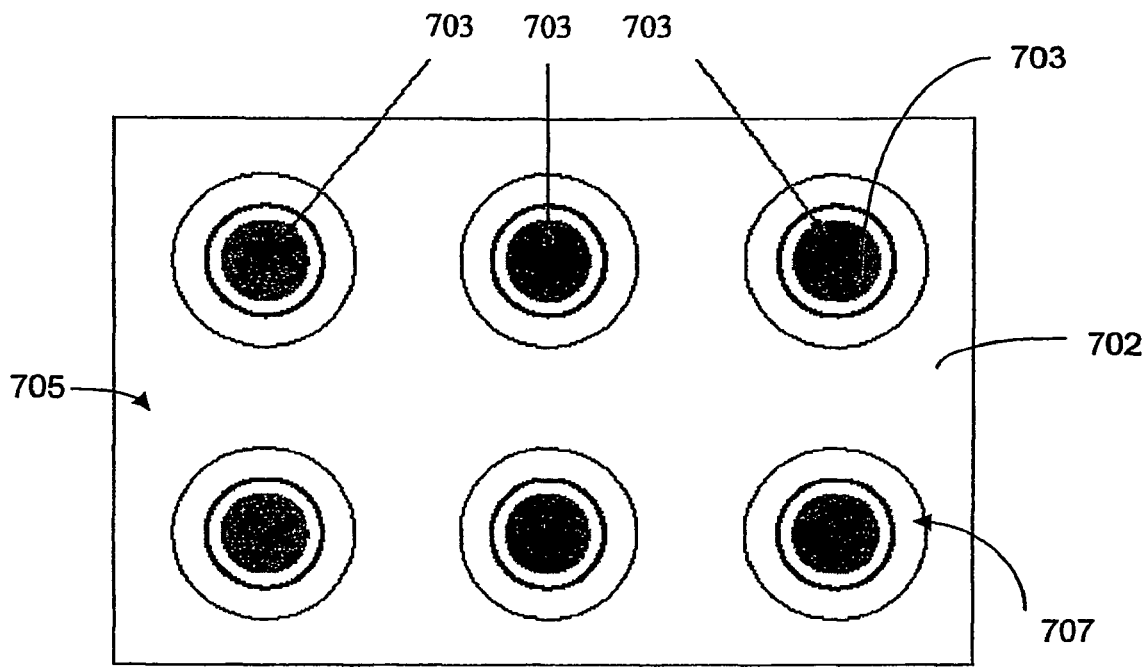
FIG. 7a is a plan view of a substrate according to the invention carrying a sensor array.
Figure 7B:
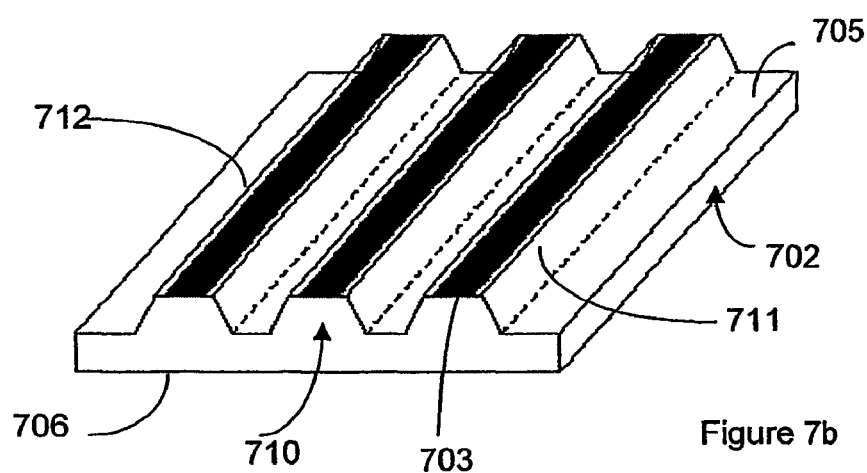
FIG. 7b is a perspective view of a substrate according to the invention having a plurality of ridges formed thereon.
Figure 8:
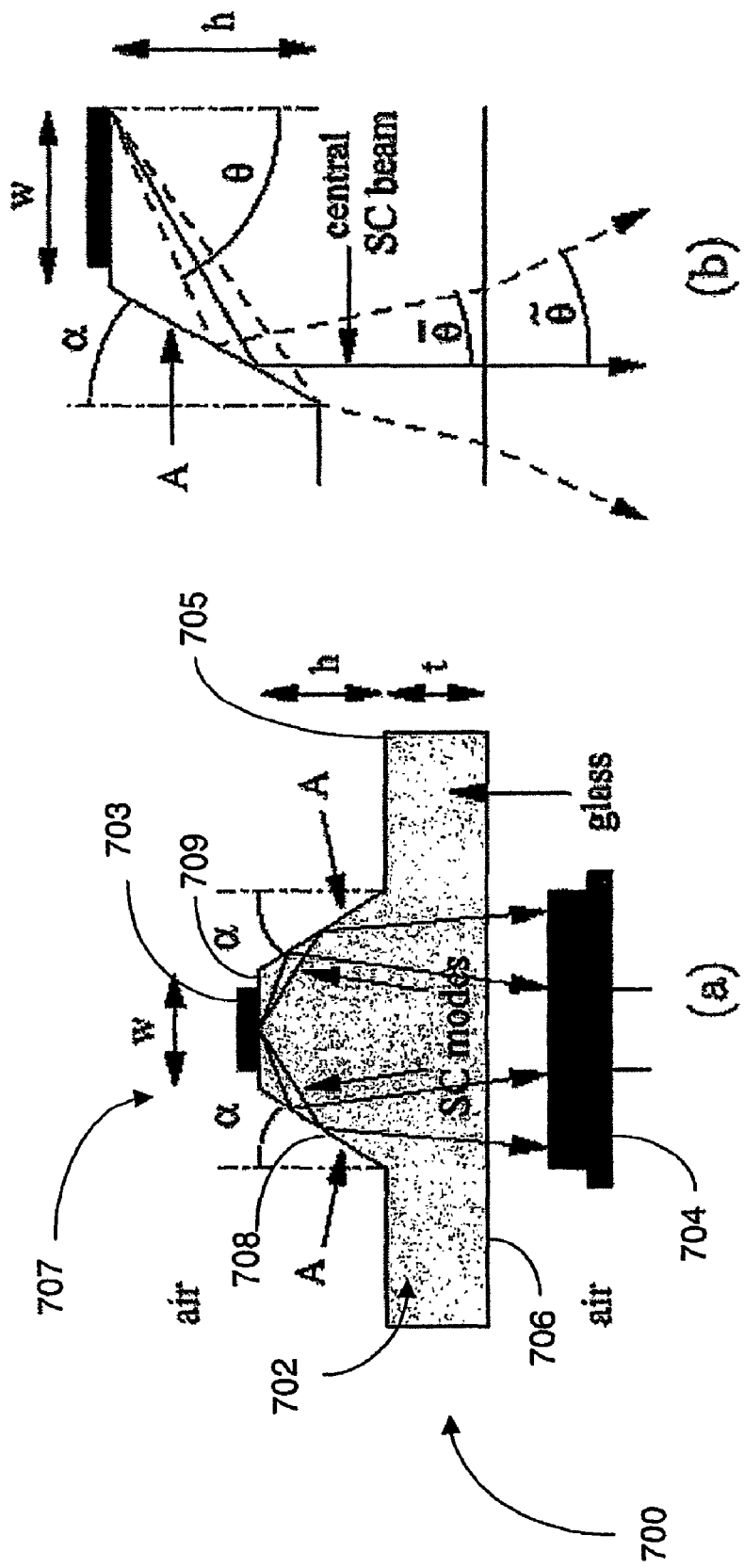
FIG. 8a is a side view of a sensor from the array of FIG. 7a, FIG. 8b is a detailed view of the sensor of FIG. 8a, FIG. 8c is graph showing the fraction of the luminescence detected by an ideal detection system as a function of its numerical aperture NA.

FIGS. 7 and 8 show a sensor device indicated generally by the reference numeral 700, which comprises a substrate 702 coated with a plurality of individual portions of luminescent material 703 sensitive to an analyte species, below which is mounted a photo detector 704 for collecting the luminescence emerging from the substrate. The detector 704 mounted below the substrate 702 comprises a CCD camera. The substrate 702 has an upper surface 705 and a lower surface 706. In the embodiment of FIG. 7a, each portion of luminescent material 703 is in the form of a spot on a frusto-conical structure 707, whereas in the embodiment of FIG. 7b the luminescent material extends along an upper surface of a number of ridges 710 provided on the upper surface of the substrate.

As shown in FIG. 7a, the upper surface 705 may be so configured to have a plurality of frusto conical structures 707 or protuberances, each structure having side walls 708 and an upper surface 709. The structures typically protrude project from the upper surface 705 of the substrate. The upper surface of the structure 709 is adapted to carry the spots 703.

As shown in FIG. 7b, the upper surface of the substrate is provided with a plurality of ridges 710, each ridge having side walls 711 extending upwardly from the upper surface of the substrate and having an upper surface 712 which carries or to which a layer of luminescent material 703 is optically coupled.

On stimulation, the luminescent material 703 will radiate light substantially in accordance with the configuration illustrated in FIG. 3. The SC modes which have an angle of propagation above the critical angle initially hit the sides wall 708 and in accordance with total internal reflection are reflected from the inner surface of the side walls downwardly towards the lower surface of the substrate 706 where they exit and are detected by the detector 704. This is illustrated in FIG. 8. It will be appreciated that in order to specifically direct the SC modes downwardly towards the detector, thereby outcoupling them from their normal path of propagation within the substrate 702, that the angle of displacement α of the side walls 708 of the conical surface of the structure 707 has to be so chosen as to ensure that the light is redirected and reflected from it straight downwards through the lower surface 706 to the detector 704. This conical surface is at the angle α to the vertical.

The principle behind this design is the total internal reflection of the SC modes radiated from the luminescent spot by the tilted interface A (708). The advantage of this configuration is two-fold. Firstly, the total internal reflection at this interface is feasible for all the SC modes and can be achieved by a proper choice of the tilt angle. Secondly, the redirected SC modes impinge on the bottom interface of the substrate at angles close to 0° which guarantees that a large fraction of the power is transmitted out of the substrate towards the detector. The disadvantage of this configuration is that the top interface of the substrate needs to be modified which makes it not directly compatible with systems employing pure planar architecture.

Although it is not intended to limit the present invention to any specific theory or analysis it may be considered that the substrate containing the luminescent spot is made of glass ($n_s=1.515$) and surrounded by air ($n_a=1.0$) both from the top and bottom. The analysis can be, however, extended to any other set of parameters.

As is shown in FIG. 3(a), the SC modes propagate in the glass substrate at angles $\theta \in <\theta_c^{as}, \theta_c^{ls}>$, where $\theta_c^{as}=\arcsin(n_a/n_s) \approx 41.3°$ and $\theta_c^{ls}=\arcsin(n_l/n_s) \approx 70.7°$ are the critical angles of the air/substrate and layer/substrate interfaces, respectively. The choice of the tilt angle can be based on various criteria. In this analysis, the requirement is that the central SC beam, i.e., the light corresponding to the SC modes propagating in the glass at an angle $\theta_{centre} \equiv (\theta_c^{as}+\theta_c^{ls})/2$, is redirected straight down upon total internal reflection from the interface A, as shown in FIG. 8b.

Simple geometrical analysis implies that the angles θ and $\overline{\theta}$, i.e. the propagation angles of the light before and after the total internal reflection from the interface A, are related by $$\overline{\theta}+\theta=2\alpha$$

Due to the fact that $\theta=\theta_{centre}$ and $\overline{\theta}=0$ for the central SC beam, the tilt angle can be calculated as $$\alpha = \frac{1}{2}\theta_{center} = \frac{1}{4}(\theta_c^{as}+\theta_c^{ls}) \approx 28°$$

Using this value of alpha, the beams corresponding to the SC modes propagating at angles $\theta_c^{as}$ and $\theta_c^{ls}$ before the total internal reflection at the interface A are propagating at angles $\overline{\theta_c^{as}}=\Delta\theta_c^{la}/2$ and $\overline{\theta_c^{ls}}=-\Delta\theta_c^{la}/2$ respectively, where $$\Delta\overline{\theta_c^{ls}}=(\theta_c^{ls}-\theta_c^{as}) \approx 29.4°$$

This means that the SC modes propagate within the angular range of $$\overline{\theta} \in \left\{-\frac{\Delta\overline{\theta_c^{la}}}{2}, \frac{\Delta\overline{\theta_c^{la}}}{2}\right\} \approx \langle-14.7°, 14.7°\rangle$$

immediately after the total internal reflection at the interface A.

When the refraction at the bottom interface of the substrate is considered, the SC beam propagating in the glass substrate at an angle $\overline{\theta}$ is found to be propagating in air below the substrate at an angle $\tilde{\theta}$ as shown in FIG. 8(b). These angles are related by the Snell law, i.e., $$n_a \sin \tilde{\theta} = n_s \sin \overline{\theta}$$

Consequently, the SC modes propagate in air below the substrate within the angular range of $$\tilde{\theta} \in \left\{-\frac{\Delta\tilde{\theta}_c^{la}}{2}, \frac{\Delta\tilde{\theta}_c^{la}}{2}\right\} \approx \langle-22.6°, 22.6°\rangle$$

This implies that all the power carried by the SC modes can be captured by a detector whose numerical aperture corresponds to the cone angle of approximately 22.6°, i.e. numerical aperture NA approximately 0.38. It will be appreciated that the performance of the sensor configuration or apparatus of the present invention gives an order of magnitude improvement within the range 0.4 to 0.6.

Figure 8C:
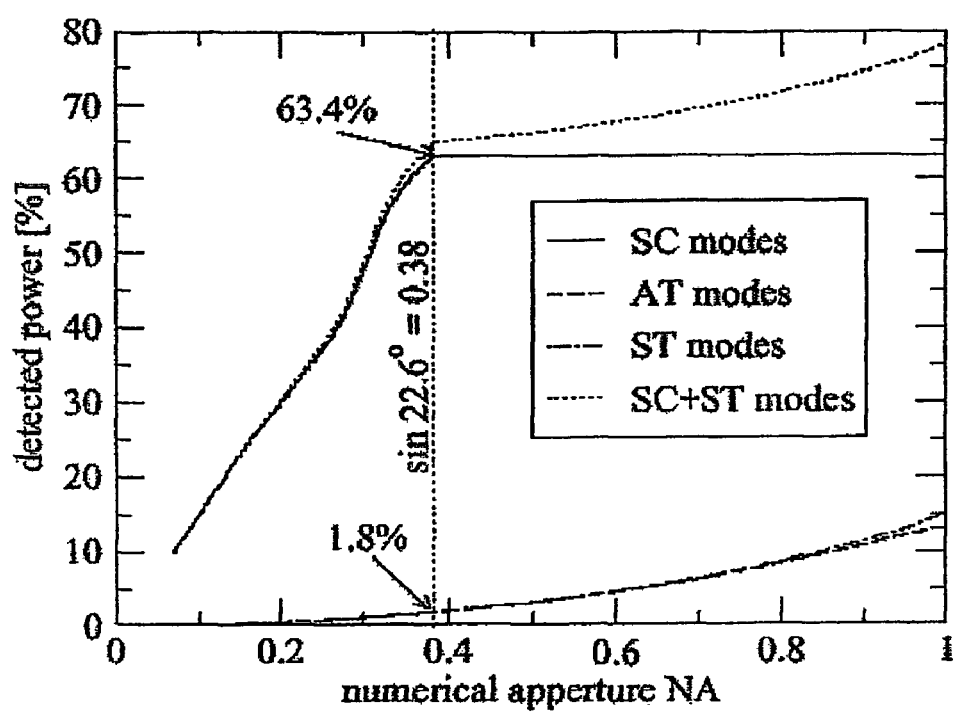

After the propagation characteristics of the luminescence have been found, it is possible to make a comparison between the luminescence capture efficiency of the conventional detection technique (see FIG. 1) and that of the improved configuration depicted in FIG. 8a. FIG. 8c shows the efficiency of the luminescence detection as a function of the numerical aperture of the ideal detection system. The dashed and dash-dotted lines correspond to the conventional technique employing detection of the luminescence radiated from the luminescent spot by means of the AT and ST modes, respectively. The solid line corresponds to the configuration employing frustrated cones (see FIG. 8).

It will be appreciated from an analysis of FIG. 6 that the conventional detection technique can capture a maximum of approximately 15% of the total emitted luminescence. However, this is possible only with a detection system characterised by NA=1. On the other hand, the detection system with NA of approximately 0.38 is able to detect approximately 63% of the total luminescence radiated from the luminescent spot if the improved detection configuration is employed to redirect the SC modes towards the detector. This clearly represents a substantial improvement. As can be seen from FIG. 8c, the efficiency of the luminescence capture achieved by the improved configuration does not increase above 63% for NA>0.38. This is because only the SC modes are considered in the evaluation of the capture efficiency (see solid line). In reality, however, the detector placed below the substrate would also detect the ST modes in addition to the SC modes. Consequently, the capture efficiency of such a system would continue increasing above NA=0.38. This is depicted by the dotted curve, which is obtained as a sum of the solid (SC modes) and dash-dotted (ST modes) curves.

When the luminescence capture efficiency of the conventional detection technique at NA of approx. 0.38 is evaluated, a value of only approximately 1.8% is found (see FIG. 8c). This means that for this given value of NA, the improved configuration provides approximately 35-fold increase in the luminescence capture efficiency. This remarkably large increase makes the configuration very attractive, despite the fact that it is not entirely compatible with the planar architecture.

In the design of the configuration with improved luminescence capture efficiency, the tilt angle, $\alpha$, plays an important role. As mentioned earlier, its evaluation can be based on various criteria. Once this angle is determined, the values of the other parameters characterising the configuration, such as W, h and t (see FIG. 8a), can be found from simple geometry. Subsequently, the values can be proportionately scaled up or down. The scaling factor is primarily determined by the target application and the technology employed in the fabrication process.

If the parameters characterising the properties of the substrate, luminescent spot or the environment covering the spot are different, the geometrical parameters of the configuration with improved luminescence capture efficiency would change. However, these parameters can easily be found by adopting the above analysis to such a system. Following the same steps as those discussed above, the tilt angle together with the angular range can be found. Furthermore, the dependence of the luminescence capture efficiency on NA, which would be similar to that shown in FIG. 8c, can be evaluated in order to determine the optimum design parameters.

Figure 9:
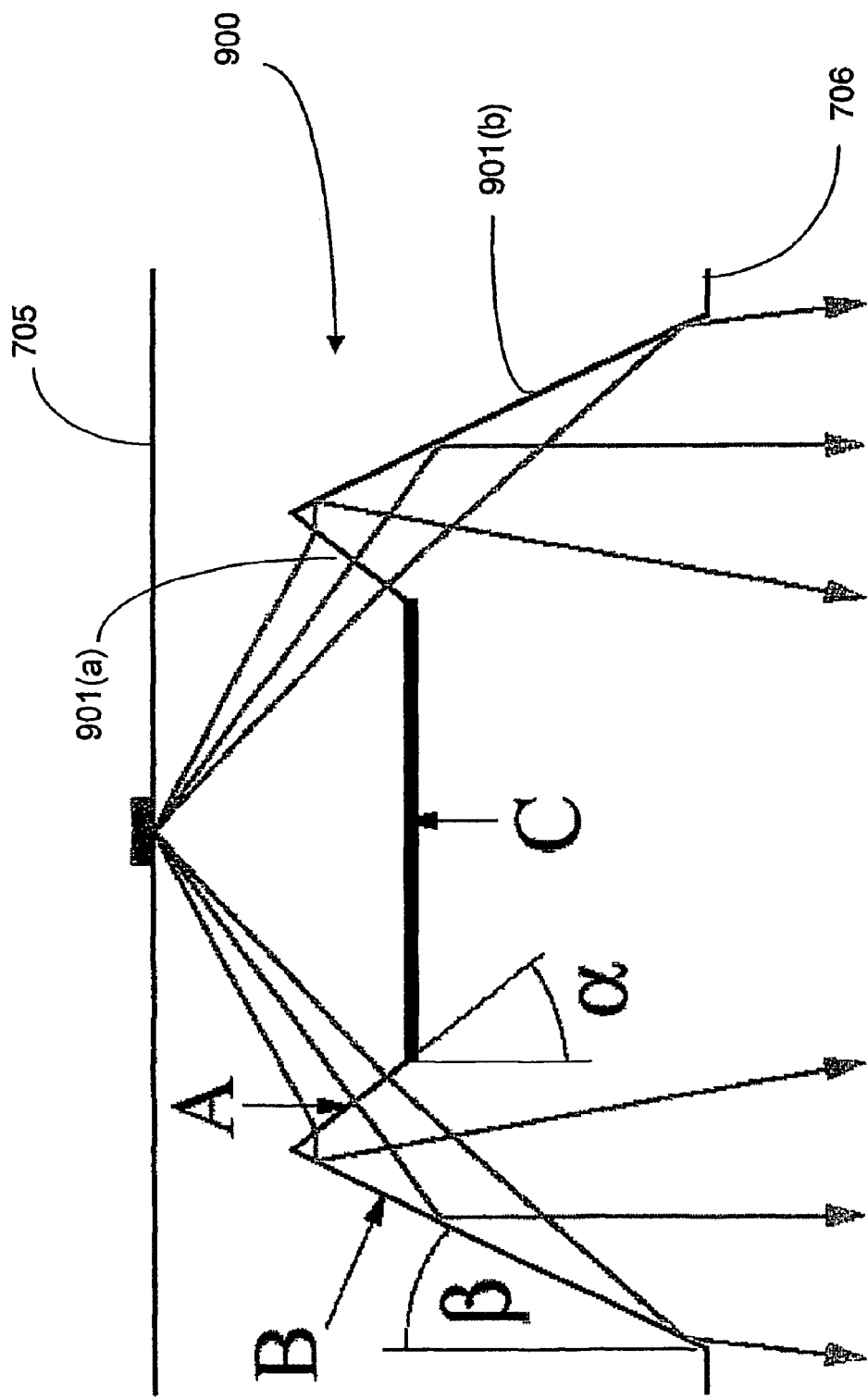
FIG. 9 is a side view of an alternative embodiment of a sensor according to the present invention.

FIG. 9 illustrates an alternative construction of substrate, identified by the reference numeral 900, in which parts similar to those described with reference to the previous drawings are identified by the same reference numerals. In this embodiment, the substrate 900 has an upper surface 705 which is planar and a low configured surface 901(a) and 901(b) which, by refraction and reflection, directs the light onto the detector 704, the light being first refracted through a lower surface 901(a) and then reflect from the lower surface 901(b) to the detector which is not shown, but will be appreciated as being positioned below the substrate. It will be appreciated that configurations such as this embodiment employ a combination of refractive and reflective elements at the bottom interface of the substrate. Total internal reflection at the bottom interface of the substrate is avoided by configuring the plane of the interface so as to decrease the angles of incidence of the SC modes to values lower than the critical angle.

This plane, through which the SC modes are refracted and transmitted outside the substrate, is denoted by A. If it is required that the detection takes place under the substrate below the luminescent spot, an additional air-substrate interface, denoted by B, can be incorporated in order to reflect the SC modes. A particular advantage of this configuration is that the top interface containing the luminescent spot is planar. This is important if the system is required to be compatible with another system employing a planar architecture. Furthermore, the orientation of the plane A is designed so as to ensure that the SC modes impinge on the plane A at angles close to 0, i.e., almost at normal incidence. This is important because the fraction T of the power transmitted through this plane, which is determined by $T \approx 1-|(n_s-n_a)/(n_s+n_a)|^2$, is large (T is approximately 96%). Although the tilted interface A provides efficient out-coupling of the SC modes outside the substrate, the modes propagate in air immediately after the interface A at large angles. This would make it difficult to detect the SC modes effectively by a detector placed under the substrate. For this reason the reflecting interface B is provided in the configuration. Its function is to redirect the SC modes towards the detector. However, a high reflectivity of this interface cannot be achieved if it is determined solely by the differences between the refractive indices of the substrate and air. For example, for $n_s=1.515$ and $n_a=1.0$, the reflectivity is approximately $|(n_s-n_a)/(n_s+n_a)|^2 \approx 4\%$ for the incident angles up to approx. 50° and is still less then approx. 50% for angles as high as 80°. Therefore, unless the reflectivity of the interface B is increased, e.g., by depositing a reflective metal layer, the poor reflectivity of this interface makes the redirection and thus the detection of the SC modes under the substrate rather ineffective.

Figure 10:
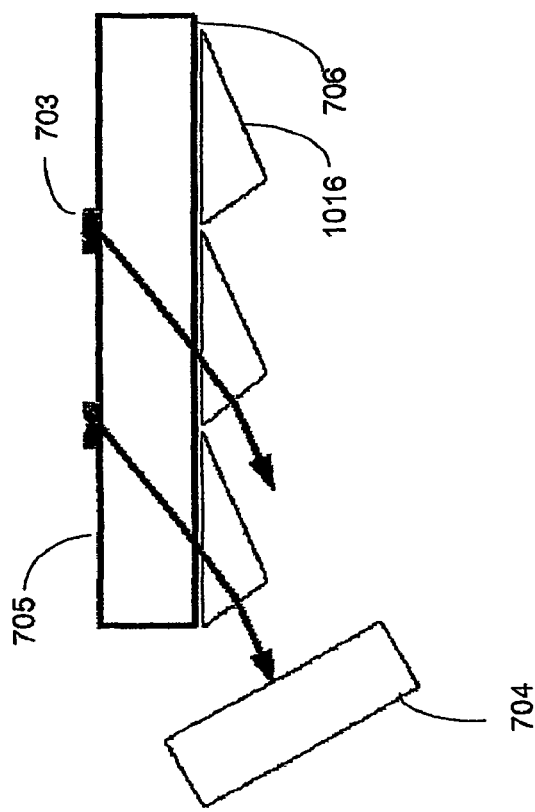
FIG. 10 is a side view of a further embodiment of a sensor according to the present invention.

FIG. 10 illustrates a construction of a sensor system or configuration, in which parts similar to those described with reference to previous drawings are identified by the same reference numerals. In this embodiment, there are mounted on the lower surface 706, macroscopic redirection elements 1016. The redirection elements, which in the example of FIG. 10 are shown in the form or a individual prisms optically coupled to the lower surface 706 of the substrate, are adapted to outcouple the SC modes which are incident on the lower surface 706 from their normal path of propagation within the substrate such that they are redirected downwardly and sidewardly towards the detector 704.

Another way of out-coupling the SC modes from the substrate and redirecting them towards the detector placed under the substrate is to use diffraction. For example, if a diffractive element, such as a grating or a more general diffractive optical element (DOE), is placed in the position where the SC modes hit the bottom interface of the substrate, the light propagated by means of the SC modes can be out-coupled and redirected towards the detector at the same time.

Figure 11:
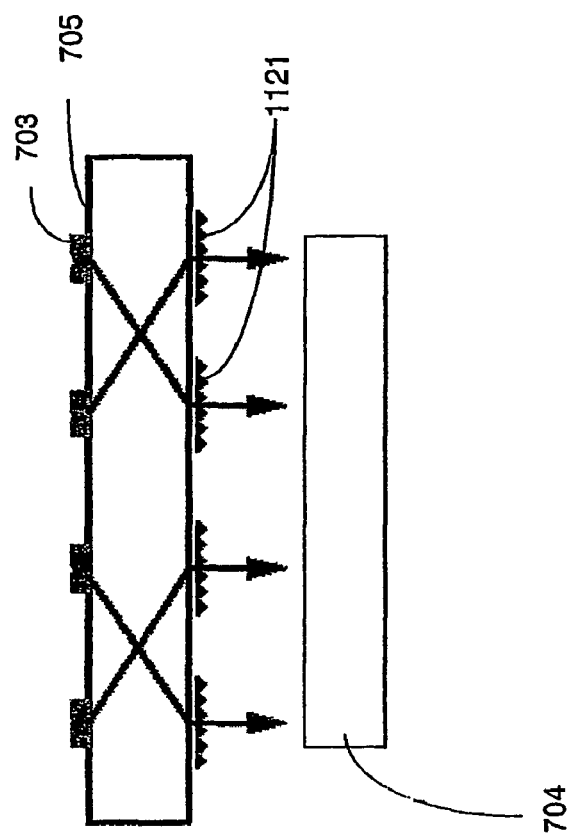
FIG. 11 is a side view of a further embodiment of a sensor according to the present invention.

Such a configuration is shown in the embodiment of FIG. 11, where there is illustrated another substrate having microscopic redirection elements 1121 provided thereon. It will be appreciated that the macroscopic 1016 and the microscopic redirection elements 1121 of the substrates of FIG. 10 and FIG. 11 will typically be integrally formed therein.

It will be appreciated that with either of these two latter configurations, the bottom of the substrate is so constructed that the luminescence emerging from the layer can be redirected by the structure as desired. When the structure is macroscopic, redirection is by way of refraction and when it is microscopic such as a diffraction grating or a general diffractive optical element, the redirection is defined by diffraction.

Figure 12:
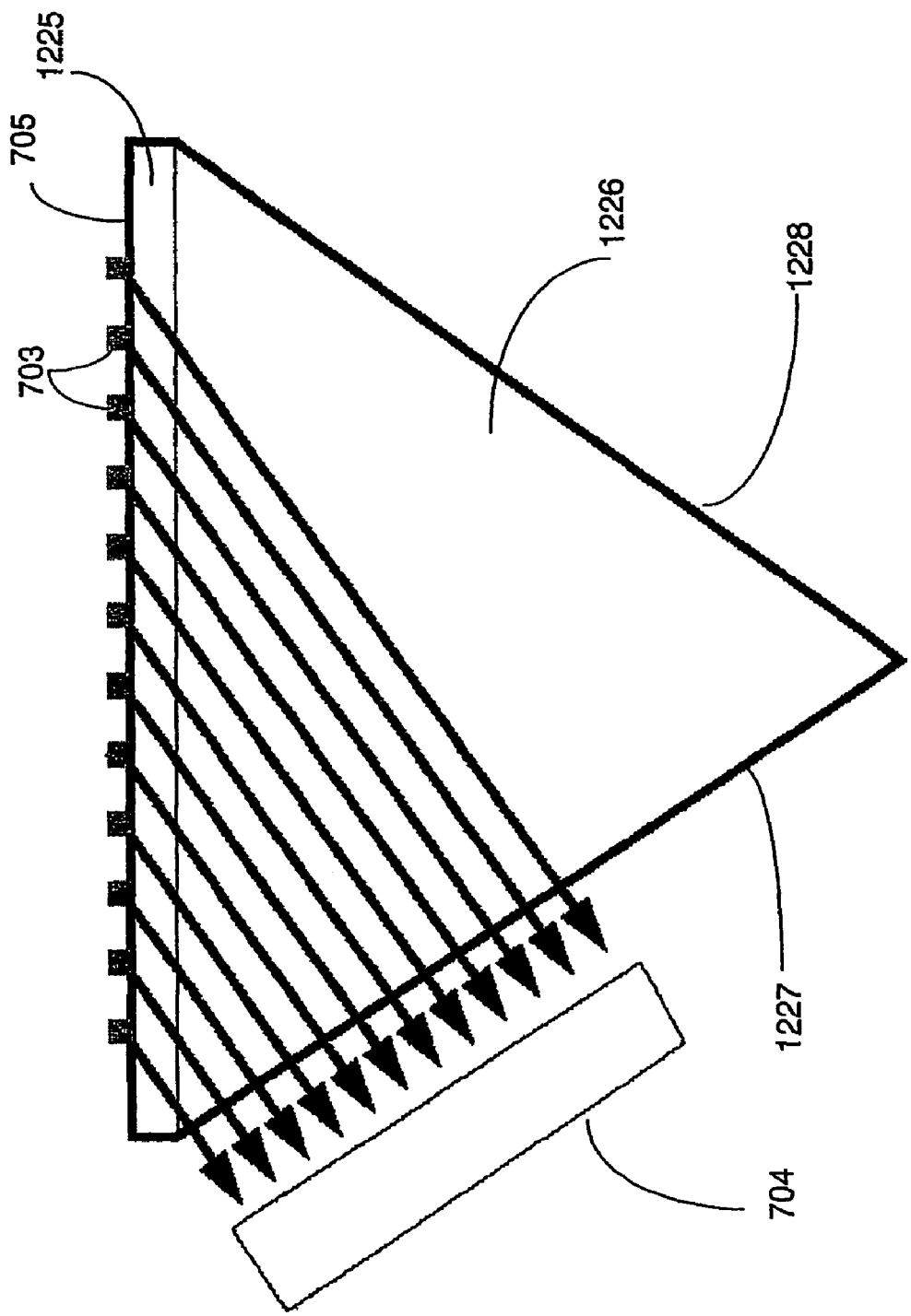
FIG. 12 is a side view of a further embodiment of a sensor according to the present invention.

Referring now to FIG. 12, there is illustrated an alternative construction of the substrate, identified by the reference numeral 1225 carrying on its upper surface 705 a dense array of spots 703. The substrate 1225 is placed on an index matching prism 1226 having lower surfaces 1227 and 1228 which are so designed that the emitted light which is being emitted from each spot within a narrow angular range, impinges on the lower surface 1227 of the prism 1226 substantially at right angles thereto so as to impinge against the detector 704. It will be appreciated that another detector could be placed on the side of the prism against and behind the other lower surface 1228. It will be appreciated that the substrate 1225 and prism 1226 may be integrally moulded.

Figure 13:
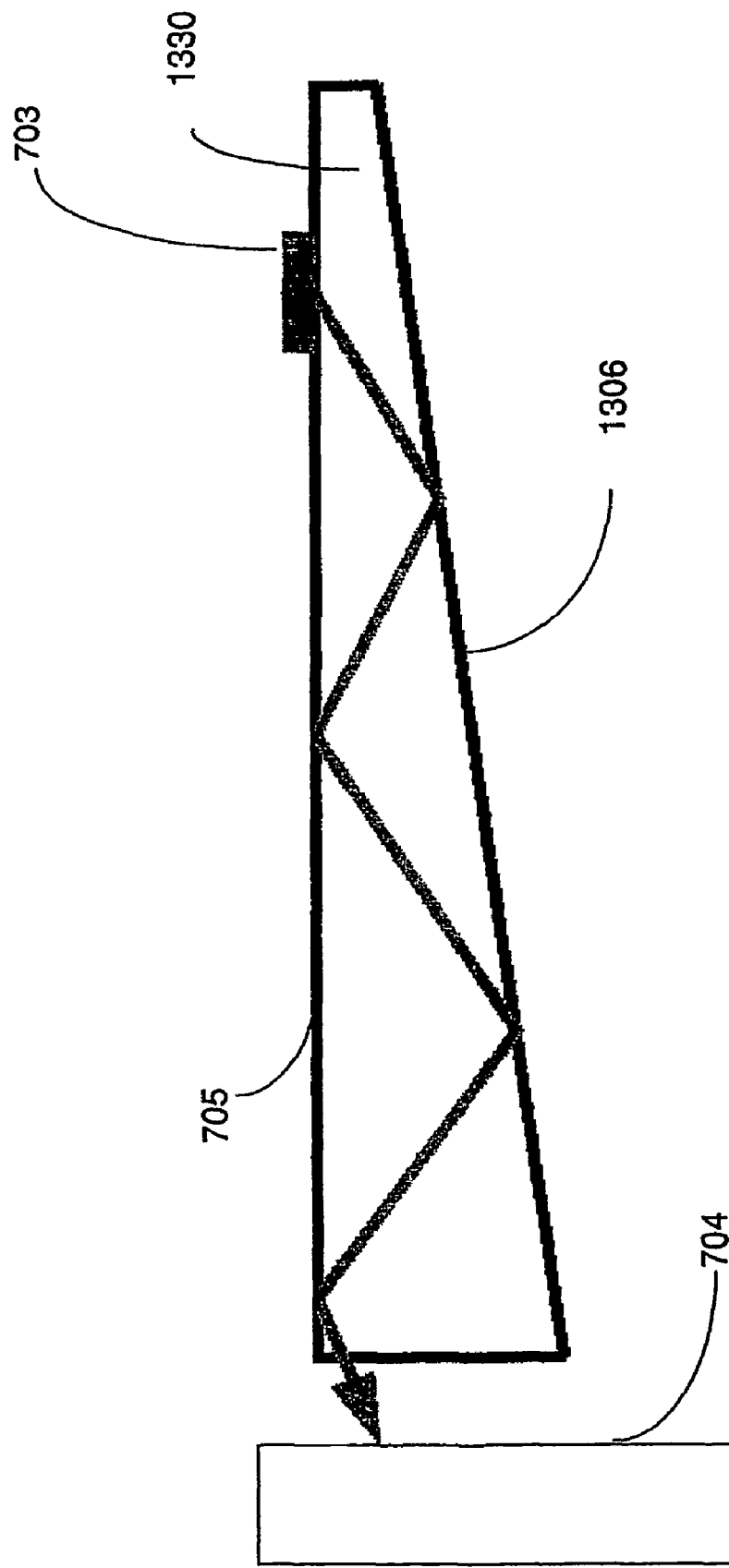
FIG. 13 is a side view of a further embodiment of a sensor according to the present invention.

Referring to FIG. 13, there is illustrated an alternative construction of substrate, identified by the reference numeral 1330, having a planar upper surface 705 and a planar lower surface 1306 which are so configured as to direct and reflect the light internally until it is directed out to the detector 704 at one end thereof. By shifting the angle of incidence of the light at the interfaces to angles greater than the critical angle, there will be little loss of the luminescent light, propagating along the critical axis of the structure, than would be achieved if both the upper and lower surface were parallel to one another as would have been detected at the edge of traditional sensing devices.

Figure 14:
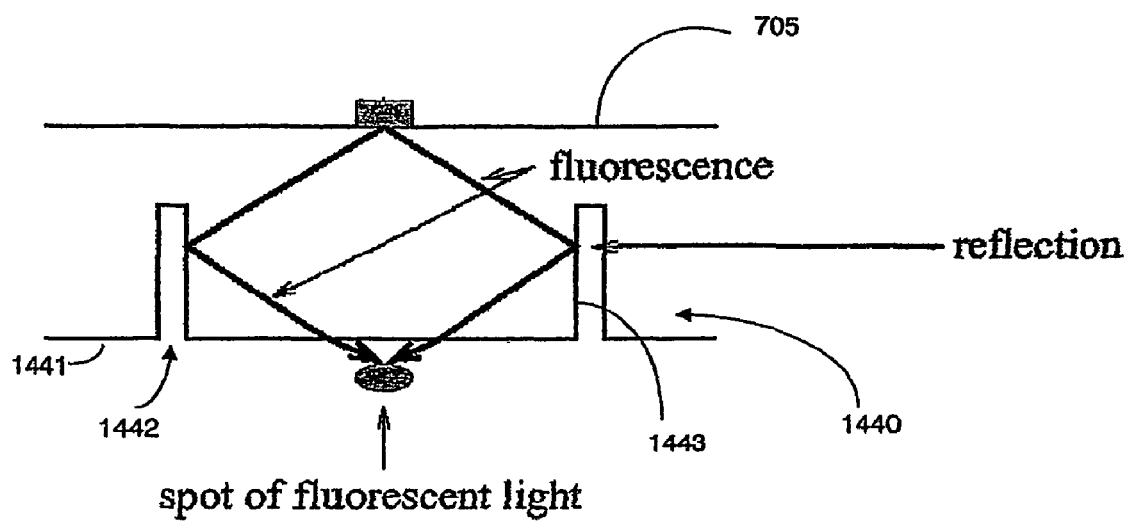
FIG. 14 is a side view of a further embodiment of a sensor according to the present invention.
Figure 15:
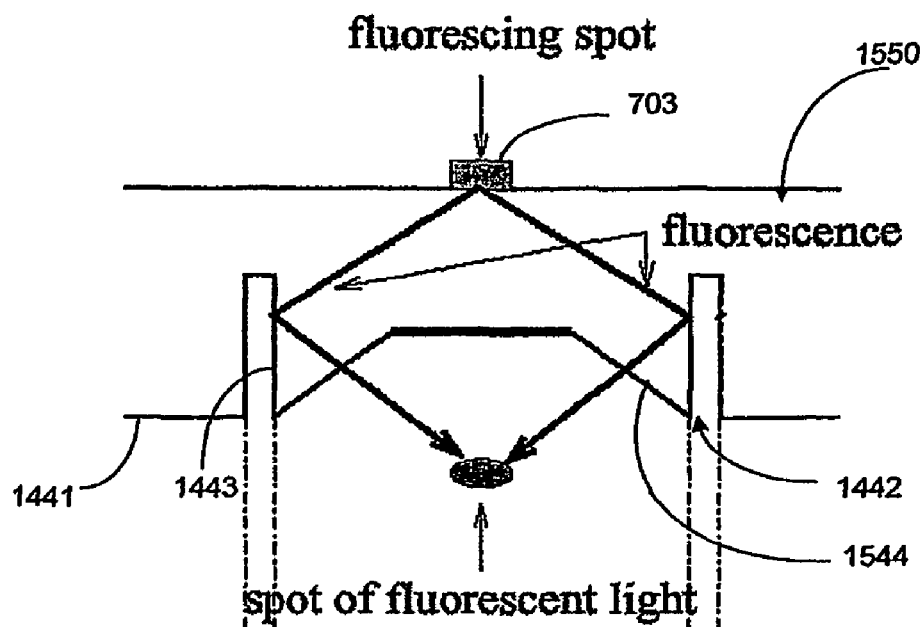
FIG. 15 is a modification to the embodiment of FIG. 14.
Figure 16:
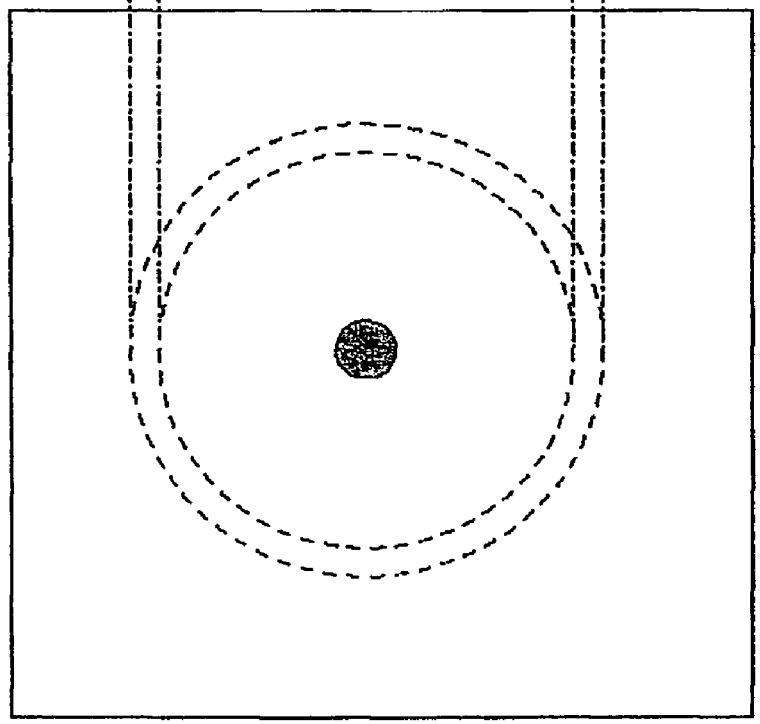
FIG. 16 is a plan view of the embodiment of FIG. 15.

Referring to FIG. 14, there is illustrated an alternative construction of substrate, identified by the reference numeral 1440 in which parts similar to those described with reference to the previous drawings are identified by the same reference numerals. The substrate 1440 has a lower surface 1441 carrying an inwardly directed annular slot 1442 carrying vertical surfaces 1443 which provide for reflection. The efficiency of such a configuration of the substrate may be improved by providing reflective coatings, such as a metal coating, on the vertical surfaces. It will also be appreciated by the person skilled in the art that the slot in effect forms a refractive index barrier which serves to reflect the light incident thereon, and that alternative configurations such as a doping of specific portions of the substrate so as to provide an equivalent reflective barrier could also be implemented Referring now to FIGS. 15 and 16, there is illustrated a still further construction of substrate, identified by the reference numeral 1550, substantially similar to the substrate 1440 except that the substrate has a lower surface 1544 intermediate the slots 1442 which provides even better transmission of the re-directed light.

With the present invention, it has been found that the configurations according to it improve luminescence collection efficiency compared with standard techniques based on direct detection above or below the substrate, it has been found that with the present invention, significantly increased amounts of light have been collected that as heretofore been possible.

Experimental Results

In order to quantify the improvement provided by the embodiments of the present invention, an experimental set up utilising the arrangement described in FIG. 8 was established. The luminescent spots were made of a sol-gel derived thin film doped with a luminescent ruthenium complex (ruthenium tris diphenyl phenanthroline or Ru(dpp)$_3$), which is characterised by the refractive index $n_f$=1.425. The chip was made from polystyrene whose refractive index over the range of wavelengths corresponding to the emission spectrum of the doped sol-gel is approximately $n_s$=1.590. The environment covering the spots was air ($n_a$=1.0). Using these parameters, the critical angles $\theta_c^{ls}$ and $\theta_c^{as}$ which play a fundamental role in the design, could be calculated. Their respective values are $\theta_c^{ls}$=63.7° and $\theta_c^{as}$=39.0°. The value of the tilt angle $\alpha$, was calculated to be approximately 26°. The configuration was designed in the axially symmetric form, and the values of the dimensions w and h were w=1 mm and h=1 mm. The chip incorporated a 2×4 array of frustrated cones on a single substrate.

The thin luminescent spots were deposited onto the substrate using a stamp fabricated from poly-dimethylsiloxane (PDMS).

Two independent experiments using two independently prepared samples were carried out in order to measure the improvement provided by the configuration employing frustrated cones. The first experiment employed a CCD camera, and the second used a detection system using a CMOS camera.

Figure 17:
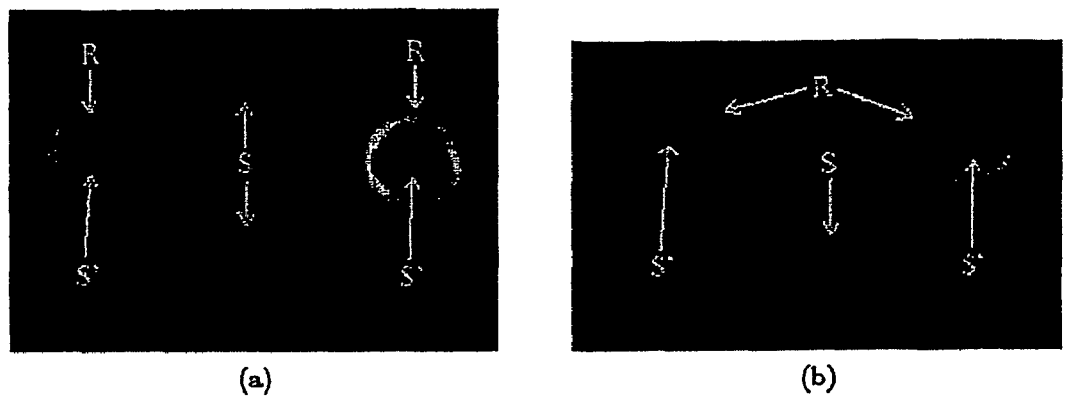
FIG. 17 shows typical examples of the images of the luminescence detected from 4 spots deposited onto a polystyrene chip according to the embodiment of FIG. 8.

It can be seen, from FIG. 17, that there are two distinct intensity profiles visible in both images. The ring-like profiles correspond to the luminescence produced by the spots which were deposited at the top of the frustrated cones. In particular, the light impinging the detector array at the area of the bright ring (R) corresponds to the SC modes of the luminescence radiated by the spot. On the other hand, the less evident grey spots (S) correspond to the ST modes of the light produced by the luminescent spots deposited onto an unmodified planar substrate, i.e., they correspond to the images of the luminescence intensity obtained by the conventional or traditional detection technique. The intensity corresponding to the ST modes radiated from the spots deposited at the top of the frustrated cones is also visible, namely in the inner area of the rings (spots denoted by S'). It can be seen that there is some non-uniformity in the intensity distribution across the image. For example, using the image in FIG. 17(a), the right ring appears to be brighter than the left one and the top spot seems to be less bright than that at the bottom. Similar features can be observed from the image in FIG. 17(b). This is due to non-uniformity of the intensity profile of the blue excitation light illuminating the luminescent spots, which could not be avoided due to an inherently divergent and spatially anisotropic character of the light produced by a LED. Furthermore, the spots S appear to be greater in size than the spots S'. This is due to a greater physical size of the luminescent spots deposited onto the planar substrate than those deposited at the top of the frustrated cones, which was caused solely by the stamping method utilised.

To estimate the improvement of the luminescence capture efficiency, the images, such as those shown in FIG. 17 were analysed. In the analysis the effects of both the non-uniformity of excitation and the size of the luminescent spot were taken into account. Details of this analysis are summarised below for the independently obtained experimental data.

CCD-Based Experiment

The analysis of the experiment employing the CCD camera is based on the image shown in FIG. 18(a). In the first step of the analysis, the total intensities detected in the areas denoted by C1-C4, A2 and A4 were obtained. The circular areas C1 and C3 represent the intensity profiles of the ST modes emitted by the luminescent spots deposited onto the unmodified (planar) substrate and detected by the CCD camera. The circular areas C2 and C4 represent the same but for the spots deposited at the top of the frustrated cones. The annulus areas A2 and A4 represent the intensity profiles of the SC modes which are emitted by the luminescent spots deposited at the top of the frustrated cones and redirected towards the detector. The corresponding total intensities are listed in Table 2, step 1.

TABLE 2

Figure 18:
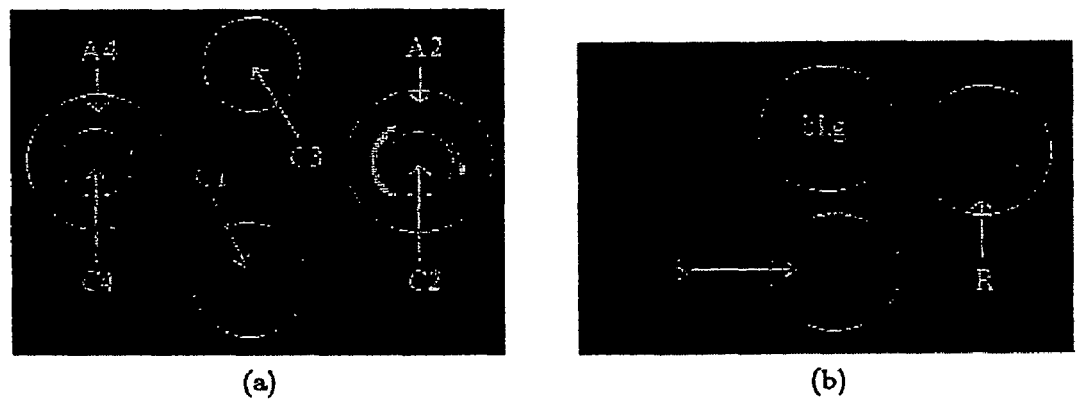
FIG. 18 shows additional images to those of FIG. 17.

Analysis of the data provided by the image in FIG. 18 (a).

total intensity [norm. units]

| step | C1 | C2 | C3 | C4 | A2 | A4 | C2 + A2 | C4 + A4 |
|---|---|---|---|---|---|---|---|---|
| 1 | 1.15 | 0.438 | 0.528 | 0.257 | 4.30 | 2.87 | 4.74 | 3.13 |
| 2 | 0.010 | 0.010 | 0.091 | 0.072 | — | — | — | — |
| 3 | 1.15 | 0.438 | 0.589 | 0.359 | 4.30 | 4.01 | 4.74 | 4.37 |
| 4 | 0.289 | 0.438 | 0.239 | 0.359 | 4.30 | 4.01 | 4.74 | 4.37 |
| $5^1$ | 1.00 | 1.52 | 0.830 | 1.24 | 14.9 | 13.9 | 16.4 | 15.1 |
| $5^2$ | 0.660 | 1.00 | 0.550 | 0.82 | 9.82 | 9.16 | 10.8 | 9.98 |
| $5^3$ | 1.21 | 1.83 | 1.00 | 1.50 | 18.0 | 16.8 | 19.8 | 18.3 |
| $5^4$ | 0.805 | 1.22 | 0.666 | 1.00 | 12.0 | 11.2 | 13.2 | 12.2 |

In the next step of the analysis, the non-uniformity of the illumination by the blue light was taken into account. This was done by requiring that the intensity in the centre of the circular areas C1-C4 be the same for each circular area. This was based on the assumption that all the spots deposited either at the top of the frustrated cones or onto the unmodified (planar) substrate have equal thickness. Indeed, in that case, the intensities of the luminescence radiated at an angle $\theta=0$ should be equal. The intensities corresponding to the centre of the circular areas C1-C4 are listed in Table 2, step 2. The intensities corresponding to all considered areas and obtained by this re-normalisation step are listen in Table 2, step 3. In the next step of the analysis, physical dimensions of the luminescent spots was taken into account. This was done by measuring the diameter d of the circular areas C1-C4 which corresponded to the diameter of the physical spots. The following values, in arbitrary units, of the diameters were found: $d_{C1}=140$, $d_{C2}=70$, $d_{C3}=110$, $d_{C4}=70$. The intensities obtained after this re-normalisation step are listed in Table 2, step 4.

In order to write the values in a form which would be more convenient for further comparison, the values obtained in the step 4 were re-normalised so that the intensities corresponding to the circular areas C1-C4 would be unity. These final values are listed in Table 2.2, steps $5^1$-$5^4$, respectively.

It will be noted that although the background intensity needed to be considered in these calculations, it was found to be zero and thus did not affect the final numerical values listed in Table 2. On the other hand, as can be seen from the image in FIG. 17(b), the background signal was quite substantial in the experiments using the CMOS camera and thus had to be considered in the calculations.

CMOS-Based Experiments

The analysis of the experiment employing the CMOS camera is based on the image shown in FIG. 18(b). As mentioned above, the background signal has to be considered in the analysis of the image shown in FIG. 17(b). Three regions of the same area are defined in the image, namely a ring-like region (R) which corresponds to the intensity of the luminescence emitted from the spot deposited at the top of the frustrated cone, a circular spot (S) which corresponds to the same but originating from the spot deposited onto the unmodified (planar) substrate, and a circular region "bkg" which provides a measure for the background signal. All the regions are of the same area and so the total intensities obtained in the following calculations are directly comparable. The total intensities measured in these regions are listed in Table 3, step 1.

TABLE 3

Analysis of the data provided by the image in FIG. 18(B).

total intensity [norm. units]

| step | S | R | bkg |
|---|---|---|---|
| 1 | 0.946 | 2.12 | 0.837 |
| 2 | 0.109 | 1.28 | 0.000 |
| 3 | 1.00 | 11.8 | 0.000 |

To enable direct comparison between the intensities emitted from the spot deposited at the top of the frustrated cone (area R) and that deposited on the planar (unmodified) substrate (area S), the intensity of the background (area "bkg") had to be subtracted. The values of the intensities after this re-normalisation step are listed in Table 3, step 2 In order to write the values in a form which would be more convenient for further comparison, the values obtained in Step 2 where re-normalised so that the intensity corresponding to the area S would be unity. The final values are listed in Table 3, step 3.

It can be seen from Tables 2 and 3 that the enhancement of the detected intensity provided by the configuration employing frustrated cones (see FIG. 8) is substantial. In particular, when the total intensity detected from a spot deposited at the top of the frustrated cone is compared to the intensity emitted by means of the ST modes, an enhancement by a factor of approximately 11-12 is obtained (see the values in columns C2+A2 and C4+A4 and the values in columns C2 and C4 in Table 2 at lines $5^2$ and $5^4$, respectively). When the total luminescence intensity detected from a spot deposited at the top of the frustrated cone is compared to the total intensity detected from a spot deposited on an unmodified (planar) substrate, an enhancement of approximately 15-20 is found (see the values in columns C2 +A2 and C4 +A4 and the values in columns C1 and C3 in Table 2.2 at lines $5^1$ and $5^3$, respectively). This factor is slightly lower (approximately 12) when the data in Table 3 is used. This difference is attributed to possible discrepancies in the thickness of the spots deposited at the top of the frustrated cones and those deposited onto the unmodified (planar) substrate, the latter being approximately 1.5 times thinner than the former, due to the imperfection of the stamping method used.

These results are experimental evidence of the level of improvement of the luminescence capture efficiency that can be achieved by employing the structure with frustrated cones in comparison to the efficiency provided by the conventional detection technique. Even though the improvement does not reach as high values as those corresponding to the ideal situation, the 10-12 fold increase in the detected intensity clearly demonstrates how attractive the improved configuration is. It is believed that this improvement factor could be further increased by providing better quality (in terms of the surface roughness) of the side walls of the structure.

It will be appreciated that the substrate and sensor configuration of the present invention provide enhanced luminescence capture from materials. Such enhancement has many applications in sensors such as environmental monitoring, biochips, DNA chips, bioluminescence, chemiluminescence and many others. The improvement enables a lower detection of substances in a medium than is available using traditional of conventional techniques. Typical implementations of the present invention will include assay kits or tools which comprises a plurality of sensing elements, each elements being adapted to detect one or more specific substances. It will be further appreciated by those skilled in the art that the application of the luminescence material that is used with the substrate of the present invention may be achieved in any of a number of different ways, and may differ for specific application or purposes. Furthermore it will be appreciated that the sensitivity of the material may be chosen specifically for particular applications, as some materials are sensitive for the presence of certain material or samples but not for others.

The words "comprises/comprising" and the words "having/including" when used herein with reference to the present invention are used to specify the presence of stated features, integers, steps or components but does not preclude the presence or addition of one or more other features, integers, steps, components or groups thereof. Similarly, the words "upper", "lower", "above", "below" etc., are not intended to limit the application of the present invention to such physical configurations.

The invention claimed is:

1. A sensor substrate (702, 900) formed from a material of a first refractive index, adapted to receive incident light emitted from a luminescence material of a second refractive index optically coupled thereto, for use in an environment having a third refractive index, the third refractive index being less than the second refractive index and the second refractive index being less than the first refractive index, the sensor substrate comprising:

an upper surface (701,710) having a plurality of integral solid frustoconical protuberances (707,710) protruding therefrom, each of the protuberances having only outer side walls extending upwardly from the upper surface of the sensor substrate and terminating in a protuberance upper surface, the protuberance upper surface being offset from the outer side walls and being substantially parallel to the sensor substrate upper surface, the protuberance upper surface being configured to operably have a luminescent material optically coupled thereto which, on stimulation, emits light downwardly through the protuberance upper surface and into the protuberance, wherein the outer walls of the protuberances are oriented relative to the protuberance upper surface such that the side wall (711) of each protuberance is vertically displaced from the upper surface at an angle substantially equivalent to one quarter the sum of the critical angles of the luminescent material/substrate interface and the environment/substrate interface so as to specifically redirect the light emitted by the luminescent material through the protuberance upper surface and received into the sensor substrate at angles which are less than the critical angle of the luminescent material/substrate interface and greater than the critical angle of the medium/substrate interface, out of the sensor substrate and towards a detector (704) provided below the protuberance upper surface, the protuberances using total internal reflection to operably redirect the light.

2. The sensor substrate of claim 1 comprising a plurality of integral protuberances (707,710).

3. The sensor substrate of claim 1 wherein the redirected light corresponds to light defined by the substrate confined (SC) modes of the light emitted into the substrate and substantially all the power carried by these modes is detectable using a detector having a numerical aperture in the range 0.3 to 0.6.

4. A sensor array comprising:
a sensor substrate (702, 900) according to claim 1, and
a biorecognition element (703) coated on the protuberance upper surface of the at least one or plurality of protuberances.

5. A sensor array according to claim 4 wherein said biorecognition element (703) is sensitive to and adapted to couple with any compatible biological sample in the medium with which the sensor is used, and once coupled a further coupling of the coupled biological sample/bio-recognition element with a luminescent tag effects the formation of the luminescent material.

6. A sensor array according to claim 4 wherein at least two protuberances are coated with different biorecognition elements.

7. A sensor comprising:
a sensor array according to claim 4; wherein the detector (704) is adapted to detect the light redirected out of the substrate (702, 900).

8. A sensor according to claim 7 wherein the detector (704) is a CMOS or CCD type detector.

9. A method for detecting the presence of a luminescent molecule comprising contacting the molecule with the array of claim 7 and detecting any luminescent light emitted by the sensor substrate.

10. The method of claim 9, wherein the luminescent material is sensitive to an analyte.

11. A luminescent sensor system comprising:
(i) a light source;
(ii) a detector (704); and
(iii) a sensor substrate comprising an upper surface having a plurality of integral solid protuberances protruding therefrom, each of the protuberances having only outer side walls extending upwardly from the upper surface of the sensor substrate and terminating in a protuberance upper surface, the protuberance upper surface being offset from the outer side walls and being substantially parallel to the sensor substrate upper surface, the protuberance upper surface being configured to operably have a luminescent material optically coupled thereto which, on stimulation from the light source, emits light downwardly through the protuberance upper surface and into the protuberance, wherein the outer side walls of the protuberance are vertically displaced relative to the protuberance upper surface at an angle substantially equivalent to one quarter the sum of the critical angles of the luminescent material/substrate interface and the environment/substrate interface so as to specifically redirect the light emitted by the luminescent material through the protuberance upper surface and received into the sensor substrate at angles which are less than the critical angle of the luminescent material/substrate interface and greater than the critical angle of the medium/substrate interface, out of the sensor substrate and, wherein the substrate is formed of a material of a first refractive index, the luminescent material of a second refractive index and the system is used in an environment having a third refractive index, the third refractive index being less than the second refractive index and the second refractive index being less than the first refractive index such that operably the light source effects an excitation of the luminescent material, the resultant luminescence being received within the substrate and directed towards the detector provided below the protuberance upper surface.

12. A luminescent sensor system comprising:
(i) a light source;
(ii) a detector (704); and
(iii) a sensor substrate formed from a material of a first refractive index comprising an upper surface having a plurality of integral frustoconical solid protuberances protruding therefrom, each of the protuberances having only outer side walls extending upwardly from the upper surface of the sensor substrate and terminating in a protuberance upper surface, the protuberance upper surface being offset from the outer side walls and being substantially parallel to the sensor substrate upper surface, the protuberance upper surface being configured to operably have a luminescent material of a second refractive index optically coupled thereto which, in use in an environment having a third refractive index, on stimulation from the light source, emits light downwardly through the protuberance upper surface and into the protuberance, wherein the outer side walls of the protuberance are vertically displaced relative to the protuberance upper surface at an angle substantially equivalent to one quarter the sum of the critical angles of the luminescent material/substrate interface and the environment/substrate interface such that the light emitted by the luminescent material through the protuberance upper surface and received into the sensor substrate at angles which are greater than the critical angle of the medium/substrate interface are reflected only once off the side walls and out of the sensor substrate such that operably the light source effects an excitation of the luminescent material, the resultant luminescence being received within the substrate and directed towards the detector provided below the protuberance upper surface.

\* \* \* \* \*

UNITED STATES PATENT AND TRADEMARK OFFICE
CERTIFICATE OF CORRECTION

PATENT NO. : 7,655,475 B2 Page 1 of 1
APPLICATION NO. : 10/470133
DATED : February 2, 2010
INVENTOR(S) : MacCraith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this

Twenty-third Day of November, 2010

David J. Kappos
*Director of the United States Patent and Trademark Office*